US010098960B2

(12) United States Patent
McDonnell et al.

(10) Patent No.: US 10,098,960 B2
(45) Date of Patent: Oct. 16, 2018

(54) POLYMER CONJUGATE

(71) Applicant: UCL Business PLC, London (GB)

(72) Inventors: Thomas McDonnell, London (GB); Anisur Rahman, London (GB); Yiannakis Ioannou, London (GB); Charis Pericleous, London (GB); Ian Giles, London (GB)

(73) Assignee: UCL BUSINESS PLC, London (GB)

( * ) Notice: Subject to any disclaimer, the term of this patent is extended or adjusted under 35 U.S.C. 154(b) by 0 days.

(21) Appl. No.: 15/090,333

(22) Filed: Apr. 4, 2016

(65) Prior Publication Data

US 2016/0287718 A1 Oct. 6, 2016

Related U.S. Application Data

(60) Provisional application No. 62/142,479, filed on Apr. 3, 2015.

(51) Int. Cl.

| | |
|---|---|
| ***A61K 38/00*** | (2006.01) |
| ***A61K 47/48*** | (2006.01) |
| ***C07K 14/775*** | (2006.01) |
| ***C07K 14/47*** | (2006.01) |

(52) U.S. Cl.

CPC .... *A61K 47/48215* (2013.01); *C07K 14/4713* (2013.01); *C07K 14/775* (2013.01); *A61K 38/00* (2013.01); *C07K 2319/21* (2013.01)

(58) Field of Classification Search

None

See application file for complete search history.

(56) References Cited

U.S. PATENT DOCUMENTS

| | | | |
|---|---|---|---|
| 7,595,292 | B2 | 9/2009 | Brocchini et al. |
| 9,005,598 | B2 | 4/2015 | Godwin |
| 2005/0004351 | A1 | 1/2005 | Marquis et al. |
| 2006/0210526 | A1 | 9/2006 | Brocchini et al. |
| 2008/0300348 | A1 | 12/2008 | Haddleton et al. |
| 2009/0214563 | A1 | 12/2009 | Kirchhofer et al. |
| 2010/0239517 | A1 | 9/2010 | Brocchini et al. |
| 2013/0252887 | A1 | 9/2013 | Beglova et al. |

FOREIGN PATENT DOCUMENTS

| | | |
|---|---|---|
| WO | 99/45964 | 9/1999 |
| WO | 2014/184564 | 11/2014 |
| WO | 2015/004038 | 1/2015 |
| WO | 2016/059377 | 4/2016 |
| WO | 2016/063006 | 4/2016 |

OTHER PUBLICATIONS

Wong et al. Clinical Feature, Diagnosis, and Management of the Antiphospholipid Syndrome, Seminars in Thrombosis and Hemostasis/ vol. 34, No. 3 2008, p. 300-304.*

Pozzi et al. (Chemical synthesis and characterization of wild-type and biotinylated N-terminal domain 1-64 of b2-glycoprotein I, Protein Science 2010 vol. 19:1065-1078.*

De Laat et al "IgG antibodies that recognize epitope Gly40-Arg43 in domain I of β2-glycoprotein I cause LAC, and their presence correlates strongly with thrombosis" *Blood*, 105:1540-1545 (Feb. 2005).

De Laat et al. "Pathogenic anti-β2-glycoprotein I antibodies recognize domain I of β2-glycoprotein I only after a conformational change" *Blood*, 107:1916-1924 (Mar. 2006).

Fishburn "The pharmacology of PEGylation: Balancing PD with PK to generate novel therapeutics" *Journal of Pharmaceutical Sciences*, 97:4167-4183 (Oct. 2008).

Ioannou et al. "A novel expression system of domain I of human beta2 glycoprotein I in *Escherichia coli" BMC Biotechnology*, 6:8, 11 pages (Feb. 2006).

Ioannou et al. "Binding of antiphospholipid antibodies to discontinuous epitopes on domain I of human β2-glycoprotein I" *Arthritis & Rheumatism*, 56:280-290 (Jan. 2007).

Ioannou et al. "In vivo inhibition of antiphospholipid antibody-induced pathogenicity utilizing the antigenic target peptide domain I of $\beta_2$-glycoprotein I: Proof of concept" *Journal of Thrombosis and Haemostasis*, 7:833-842 (May 2009).

Iverson et al. "Use of single point mutations in domain I of β2-glycoprotein I to determine fine antigenic specificity of antiphospholipid autoantibodies" *Journal of Immunology*, 169:7097-7103 (Dec. 2002).

Iverson et al. "Anti-β2 glycoprotein I (β2GPI) autoantibodies recognize an epitope on the first domain of β2GPI" *Proc Natl Acad Sci USA*, 95:15542-15546 (Dec. 1998).

McDonnell et al. "Development of a high yield expression and purification system for domain I of beta-2-glycoprotein I for the treatment of APS" *BMC Biotechnology*, 15:104, 11 [ages (Nov. 2015).

Nayfe et al. "Seronegative antiphospholipid syndrome" *Rheumatology*, 52:1358-1367 (Aug. 2013).

Pericleous et al. "Evaluating the conformation of recombinant domain I of β2-glycoprotein I and its interaction with human monoclonal antibodies" *Molecular Immunology*, 49:56-63 (Oct. 2011).

Polytherics "TheraPEG™-DI: A novel approach to treating anti-phospholipid syndrome (APS)" slide presentation of 10 pages on Apr. 14, 2014.

Schumaker et al. "In situ maleimide bridging of disulfides and a new approach protein pegylation" *Bioconjugate Chemistry*, 22:132-136 (Jan. 2011).

Smith et al. "Protein modification bioconjugation, and disulfide bridging using bromomaleimides" *Journal of the American Chemical Society*, 132:1960-1965 (Feb. 2010).

Steinkasserer et al. "Complete nucleotide and deduced amino acid sequence of human β2-glycoprotein I" *Biochemical Journal*, 277:387-391 (Jul. 1991).

* cited by examiner

*Primary Examiner* — Jeanette M Lieb

(74) *Attorney, Agent, or Firm* — Nixon & Vanderhye P.C.

(57) ABSTRACT

The present invention concerns a conjugate of a domain I β2GP1 polypeptide with a water-soluble polymer, wherein the polymer is bound via two cysteine residues derived from a disulfide bridge in the domain I β2GP1 polypeptide.

21 Claims, 8 Drawing Sheets

Specification includes a Sequence Listing.

```
         10         20         30         40         50         60
MKHHHHHHPM SDYDIPTTEN LYFQGLNDIF EAQKIEWHEG SGSGSIEGRM GRTCPKPDDL
         70         80         90        100        110
PFSTVVPLKT FYEPGEEITY SCKPGYVSRG GMRKFICPLT GLWPINTLKC TPR
```

POLYMER CONJUGATE

This application claims priority benefit of provisional Application No. 62/142,479, filed Apr. 3, 2015; the content of which is incorporated by reference herein.

This invention relates to novel polymer conjugates, and a process for their preparation.

Antiphospholipid Syndrome (APS) is an autoimmune disease characterised by vascular thrombosis and/or pregnancy complications and miscarriage in patients and is a significant cause of mortality and morbidity. It is also the leading cause of strokes in patients under 50 years of age (Andreoli L, et al., *Arthritis Care and Research* (Hoboken). 2013 November; 65(11):1869-73; Ioannou Y, et al., *Journal of thrombosis and haemostasis: JTH* 2009, 7(5):833-842; Lambrianides A, et al., *J Immunol* 2010, 184(12):6622-6628; Ioannou Y, et al., *Arthritis and rheumatism* 2007, 56(1):280-290)

According to the current Sydney classification criteria updated in 2006, APS is diagnosed in a patient exhibiting at least one clinical feature including vascular thrombosis and pregnancy morbidity, and one laboratory feature characterised by the presence of persistent antiphospholipid antibodies (aPLs) (Miyakis S et al., J Thromb Haemost 2006; 4:295-306). aPLs present in APS are a heterogeneous population of auto-antibodies (Alessandri, C et al., *Autoimmunity reviews* 2011, 10(10):609-616) that bind a range of antigens, in particular beta-2-glycoprotein I (β2GPI) (Ioannou Y, et al., *Arthritis and rheumatism* 2007, 56(1):280-290; Galli M, et al., *Lancet* 1990, 335(8705):1544-1547; McNeil H, et al., *Proc. Nat. Acad. Sci.* 1990, 87(11):4120-4124). Among the heterologous population of aPLs, β2GPI is regarded as the most important antigen in APS (de Laat B et al., *Blood* 2006; 107:1916-24).

β2GPI is a 50 kilodalton plasma glycoprotein that displays several properties defining an anticoagulant, such as inhibition of contact activation of the intrinsic coagulation pathway, platelet prothrombinase activity, and ADP-induced platelet activation (Roubey (1996) Arthritis Rheum. 39:1444). The amino acid sequence of β2GPI has been determined (Lozier et al. (1984) PNAS USA 81:3640; Steinkasserer A, et al., *Biochemical Journal.* 1991; 277(Pt 2):387-391) and shown to be composed of five homologous domains numbered 1 to 5 from the N-terminus. Domains I-IV are composed of approximately 60 amino acids that contain a motif characterised by a framework of four highly conserved cysteine, proline and tryptophan residues (Steinkasserer A, et al., *Biochemical Journal.* 1991; 277(Pt 2):387-391). Each domain is characterised by independent folding, in which the four cysteine residues form two internal disulfide bridges. Domain V is composed of 82 amino acids with 6 cysteine residues, which form three internal disulfide bridges.

Anti-β2GPI antibodies have been closely associated with thrombosis implying a significant role of these antibodies in the pathogenesis of the disease (Pierangeli S S, et al., *Circulation research* 2001, 88(2):245-250; Pierangeli S S, et al., *Circulation* 1996, 94(7):1746-1751). It was not until 2006 however, when the modified classification criteria were published, that IgG and IgM antibodies to β2GPI were added to the definition of APS. Among anti-β2GPI antibodies, it has been demonstrated that it is those that bind specifically to domain I were associated with thrombosis more than their counterparts targeted to other domains of β2GPI (de Laat et al, 2005, Blood, 105, 1540-1545). In contrast, anti-β2GPI antibodies derived from patients without clinical features of APS do not preferentially bind domain I, but are directed against other domains of β2GPI (de Laat B et al., *Blood* 2005; 105:1540-5). Extensive mutational studies on the DI domain have also demonstrated that aPLs bind a conformational epitope on domain I, centred around the area of residues spanning amino acids 39 to 43, and the area around a doublet at amino acids 8 and 9 (Ioannou Y, et al., *Journal of thrombosis and haemostasis: JTH* 2009, 7(5):833-842). To date however, anti-domain I antibodies have not been added to the established diagnostic guidelines for APS.

It has also become apparent that a group of patients with clinical manifestations highly suggestive of APS but who test negative for aPLs using the current (2006) laboratory criteria. This patient group has been referred to as having seronegative APS (SNAPS). Like classical APS, SNAPS can exhibit accelerated progression resulting in multi-organ failure and other life-threatening medical conditions, but are often mis- or undiagnosed and therefore not treated. Further research has revealed that some patients with presumed SNAPS actually do have circulating antibodies which can be detected by assays not included in the current criteria ("non-criteria" aPLs). In particular, both IgA anti-β2GPI and IgG anti-D1 antibodies have been described in such patients (Cousins et al., Ann Rheum Dis 2015 in press). Various studies described the association between the exclusive expression of IgA anti-β2GPI antibody and the clinical manifestations of APS (Diri E, et al., *Lupus* 1999; 8:263-8; Bertolaccini M L, et al., *J Rheumatol* 2001; 28:2637-43; Petri M. *Lupus* 2010; 19:419-23; Danowski A, et al., *J Rheumatol* 2006; 33:1775-9). For instance, in one study women with unexplained recurrent spontaneous abortions and fetal death solely expressed the IgA isotype of anti-β2GPI antibody and negative for LA (Danowski A, et al., *J Rheumatol* 2006; 33:1775-9).

Current treatment for APS patients is long-term anticoagulation with warfarin or heparin, which are a non-specific vitamin K dependent coagulation blocking agent and an activator of anti-thrombin III respectively. These treatments lack efficacy in all cases and carry a significant risk of side-effects such as haemorrhage (Khamashta M A, et al., *The New England Journal of Medicine* 1995, 332(15):993-997). Moreover, warfarin is also a known teratogen and thus its use is contraindicated in pregnancy, particularly in the first trimester.

There is thus a pressing need to develop new detection systems and targeted therapies for anti-β2GPI mediated conditions.

In view of the evidence showing that the immunodominant epitope for the majority of circulating pathogenic APLs is the N-terminal domain I of β2GPI, a number of studies have focussed on the use of recombinant domain I as a potential future therapeutic agent for APS. These studies have shown that recombinant domain I, and a variant of domain I known as DI(D8S/D9G), inhibit the binding of aPLs derived from patients with pregnancy loss as well as aPLs from patients with thrombosis to immobilised native antigen in a fluid-phase inhibition ELISA, and this inhibition is greater with the DI(D8S/D9G) variant (Ioannou Y et al., *Arthritis Rheum* 2007; 56: 280-90). Follow-up studies in a mouse model of APS showed that recombinant domain I and DI(D8S/D9G) also inhibit in vivo aPL-induced venous thrombosis formation, supporting the hypothesis that an antigenic aPL-binding peptide has the potential to ameliorate aPL-induced pathogenicity in vivo (Ioannou Y et al., *Journal of thrombosis and haemostasis: JTH* 2009, 7(5): 833-842).

WO99/64595 describes domain I β2GPI polypeptides and their use for detecting and treating APS. According to the authors, the size of the domain I β2GPI polypeptide may vary widely, with amino acid sequences as small as a 6-mer said to be able to specifically bind to a β2GPI-dependent aPL. In the Examples, the majority of domain I peptide fragments did not inhibit binding of β2GPI-dependent aPL to β2GPI. The fragments that did inhibit binding peptides were found to cluster around the two sets of disulfide linked cysteines present in domain I, and it was hypothesised that these disulfide linked cysteines may create structures that are recognised by anti-β2GPI antibodies. Conjugates of domain I β2GPI polypeptides with a carrier or label are also disclosed. In some embodiments, the domain I β2GPI polypeptide is conjugated via a cysteine sulfhydryl group activated by reducing the disulphide bond, resulting in a thioether linkage in the conjugate. However, conjugation to cysteine residues necessitates reduction of the disulfide bond, potentially leading to structural changes and loss of the conformational epitope recognised by domain I anti-β2GPI antibodies.

Many therapeutically active molecules, for example proteins and peptides, do not possess the properties required to achieve efficacy in medical use. For example, some molecules which might find utility as active therapeutic agents in medicines are systemically toxic or lack optimal bioavailability and pharmacokinetics. When proteins clear from the blood circulation quickly they typically have to be administered to the patient frequently. Frequent administration further increases the risk of toxicity, especially immunologically derived toxicities.

Domain I is a small protein domain, having a molecular weight of about 7 kDa. As such, it has a short half-life in vivo. Accordingly, while Domain I has previously been shown to inhibit binding of β2GPI-dependent aPL to β2GPI, its short half-life means that it is not a viable therapeutic option. In addition, it is prone to aggregation, making it difficult to produce in large quantities.

Water soluble, synthetic polymers, particularly polyethylene glycol, PEG, are widely used to conjugate therapeutically active molecules such as proteins. The conjugation of PEG is commonly known as "PEGylation", and many PEGylating reagents are known, for example from WO 99/45964, WO 2005/007197, and WO 2009/047500. These PEGylating reagents have been shown to alter the pharmacokinetics of therapeutic proteins favourably by prolonging circulation time and decreasing clearance rates by increasing the effective size of the protein, decreasing systemic toxicity, and in several cases, displaying increased clinical efficacy. However, it is commonly found that PEGylation impairs the pharmacological activity of the protein, resulting from loss in binding affinity due to steric interference with the drug-target binding interaction (Fishburn C S. J Pharm Sci. 2008 October; 97(10):4167-83). It is also commonly found that PEGylation can reduce the intrinsic in vivo activity of some proteins by shielding the protein from the substrate or the target/receptor. This loss of potency is offset by the prolonged circulation time, and thus the combination of decreased activity at the target receptor or enzyme with increased plasma half-life can translate to increased in vivo efficacy. The level of in vivo efficacy shown for a PEGylated molecule depends on the balance between the pharmacodynamic (PD) and pharmacokinetic (PK) properties of the conjugate.

We have now found that, surprisingly, PEGylated-Domain I retains the ability to inhibit binding of anti-β2GPI antibodies to β2GPI at levels at least as efficacious as those shown by the unconjugated protein.

Accordingly, the present invention provides a conjugate of a domain I β2GP1 polypeptide with a water-soluble polymer, wherein the polymer is bound via two cysteine residues derived from a disulfide bridge in the domain I β2GP1 polypeptide.

The conjugates according to the invention are expected to display favourable pharmacokinetics due to prolonged circulation time and decreased clearance rate. However, PEGylation would normally be expected to reduce the ability of Domain I to inhibit binding of anti-β2GPI antibodies to β2GPI due to the shielding effect of the polymer.

In particular, WO99/64595 discloses that all but two of the peptides tested which inhibited binding of anti-β2GPI antibodies to β2GPI were clustered around the two sets of disulfide linked cysteines present in domain I. The two peptides that were not so clustered were also the poorest at inhibiting. It was therefore concluded that these disulfide linked cysteines may create structures that are recognized by anti-β2GPI antibodies. As such, it is therefore quite unexpected that PEGylation of domain I polypeptides across the disulfide bonds does not result in loss of anti-β2GPI antibody binding, particularly given the role of the disulfide bonds in forming the conformational epitope and their position within the cluster of antibody binding sites.

The unexpected finding that PEGylated-domain I polypeptides retain anti-β2GPI antibody binding inhibitor activity at levels at least as efficacious as those shown by the unconjugated protein markedly alters the balance between the pharmacodynamic and pharmacokinetic properties of the conjugate. Conjugates according to the invention thus require less frequent dosing and at lower dosages, making the conjugates particularly suitable for treating autoimmune disorders such as APS where a prolonged inhibitory effect is desired, while reducing the risk of toxicity, particularly immunologically derived toxicity. Minimising toxicity is especially important in APS because the aim of treatment is to prevent clinical events (thrombosis, stroke and pregnancy loss) rather than to treat symptoms. Currently, many patients with APS are taking long-term warfarin despite the fact that they are asymptomatic. There would be a clear benefit in using a targeted therapy with fewer adverse effects than anticoagulation in this scenario. Enhanced solubility and stability of domain I can also be achieved.

Throughout this Specification and claims, a domain I polypeptide should be understood to include any polypeptide comprising or consisting of the amino acid sequence of β2GPI domain I, and any analogue thereof, which has the ability to specially bind to an anti-domain I β2GPI antibody.

The complete polynucleotide and amino acid sequence of human β2GPI is disclosed in the literature, for example Steinkasserer A, et al. *Biochemical Journal.* 1991; 277(Pt 2):387-391, and are shown in FIG. 2 of that reference. The polynucleotide and polypeptide sequences of β2GPI are also publicly available in the literature, in the GenBank (Accession No. X58100) and Uniprot Databases (http://www.uniprot.org/) under accession number P02749.

The amino acid sequence of human β2GPI (326 amino acids) is also disclosed herein as SEQ ID NO: 1. In one embodiment, the domain I β2GP1 polypeptide sequence used in the present invention comprises or consists of amino acids 1 to 63 of the amino acid sequence set out SEQ ID NO: 1.

In another embodiment, the domain I β2GP1 polypeptide sequence used in the present invention comprises or consists of the amino acid sequence set out SEQ ID NO: 2. In a further embodiment, the domain I β2GP1 polypeptide sequence may comprise or consist of the amino acid sequence set out in SEQ ID NO: 3. SEQ ID NO: 2 shows the amino acid sequence of domain I of human β2GP1. SEQ ID NO: 3 shows the amino acid sequence of a variant of domain I of human β2GP1 sequence known as "D8/D9" or "DI (D8S/D9G)".

The domain I β2GP1 polypeptide used in the present invention may also optionally be modified by the addition of one or more amino acids at the N or C terminus of the chain. For example, the N-terminal end preferably comprises a non-native methionine residue immediately 5' to the domain I β2GP1 polypeptide sequence. The additional methionine residue has been found to be important for recombinant expression.

The domain I β2GP1 polypeptide may additionally comprise one or more of the amino acid residues flanking the core sequence of amino acids 1 to 63 of the amino acid sequence set out SEQ ID NO: 1. For example, the C-terminal end of the domain I β2GP1 polypeptide may comprise one or more amino acids of the domain I-domain 2 inter-linker region, for example amino acid 64 (Val) or amino acids 64 and 65 (Val Cys) of SEQ ID NO: 1.

For example, the domain I β2GP1 polypeptide disclosed therein may also comprise (or consist of, or consist essentially of) any of the following: (a) amino acid 1 to amino acid 63 of SEQ ID NOs: 2 or 3; (b) amino acid 2 to amino acid 63 of SEQ ID NOs: 2 or 3; (c) amino acid 1 to amino acid 64 of SEQ ID NO: 1; (d) amino acid 2 to amino acid 64 of SEQ ID NO: 1; (e) amino acid 1 to amino acid 65 of SEQ ID NO: 1; (f) amino acid 2 to amino acid 65 of SEQ ID NO: 1; (g) amino acid 1 to amino acid 68 of SEQ ID NO: 1; or (h) amino acid 2 to amino acid 68 of SEQ ID NO: 1.

The domain I β2GP1 polypeptide used in the present invention may optionally also include a polyhistidine tag, in which a number of histidine residues, for example 2 or more, for example up to 12, preferably up to 9, more preferably up to 6, histidine residues may be introduced. The polyhistidine tag, when present, may be present at the N or C terminus of the domain I β2GP1 polypeptide, or elsewhere along the main chain.

The term "analogue" used in relation to the domain I β2GP1 polypeptide refers to functional portions and derivatives of the domain I β2GP1 sequence shown in SEQ ID NOs: 2 or 3, and any polypeptide substantially homologous thereto, that differs by the substitution, insertion or deletion of one or more amino acids, but that has substantially the same activity or function as the unmodified sequence or partial sequence, i.e., the ability to inhibit binding of anti-β2GPI antibodies to β2GPI. Methods for testing the activity or function of analogues of the domain I β2GP1 polypeptides are well known in the art (such as the standard β2GPI ELISA published by Ioannou et al., *BMC biotechnology* 2006, 6:8) and are also described in the Examples below.

Derivatives of domain I β2GP1 polypeptides also include sequences from other biological sources such as mammals, birds (for example chicken), insects, reptiles or amphibian. Exemplary sequences of the β2GP1 protein from other species are contained in the UniProt Database, for example *Mus musculus*—Mouse (Q01339), *Canis familiaris*—Dog (P33703), *Bos taurus*—Bovine (P17690) and *Rattus norvegicus*—Rat (Q5I0M1).

The term "substantially homologous" as used herein denotes a characteristic of an amino acid sequence, wherein a selected amino acid sequence has at least about 70 or about 75 percent sequence identity as compared to a selected reference amino acid sequence. Preferably the amino acid sequence has a sequence identity of at least 80%, more preferably at least 90% and most preferably at least 95% compared to a selected reference amino acid sequence. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence, for example using sequence comparison algorithms well-known to those of skill in the art, such as, the FASTA program analysis described by Pearson and Lipman (1988) and the gapped BLAST algorithm (e.g., Altschul et al. Nucleic Acid Res. (1997)25: 3389) which weights sequence gaps and sequence mismatches according to the default weightings provided by the National Institutes of Health/NCBI database (Bethesda, Md.; see www.ncbi.nlm.nih.gov/cgi-bin/BLAST/nph-newblast).

Preferably any amino acid changes in the polypeptide sequence are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, and valine; glycine, and alanine; asparagine and glutamine; and serine, threonine, phenylalanine, and tyrosine. Other groups of amino acids that may represent conservative changes include (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Amino acids may be classified according to the nature of their side groups. Amino acids with nonpolar alkyl side groups include glycine, alanine, valine, leucine, and isoleucine. Serine and threonine have hydroxyl groups on their side chains, and because hydroxyl groups are polar and capable of hydrogen bonding, these amino acids are hydrophilic. Sulfur groups may be found in methionine and cysteine. Carboxylic acid groups are part of the side chain of aspartic acid and glutamic acid, which because of the acidity of the carboxylic acid group, the amino acids are not only polar but can become negatively charged in solution. Glutamine and asparagine are similar to glutamic acid and aspartic acid, except the side chains contain amide groups. Lysine, arginine, and histidine have one or more amino groups in their side chains which can accept protons, and thus these amino acids act as bases. Aromatic groups may be found on the side chains of phenylalanine, tyrosine, and tryptophan. Tyrosine is polar because of its hydroxyl group, but tryptophan and phenylalanine are non-polar. A polypeptide may also, or alternatively, contain non-conservative changes.

It is understood that a domain I β2GP1 polypeptide may bind to an anti-β2GP1 antibody via a conformational epitope. Accordingly, in some embodiments, a domain I β2GP1 polypeptide used in the present invention comprises (a) amino acid 39 of SEQ ID NO: 2 (Arg); (b) amino acids 39 to 43 of SEQ ID NO: 2 (Arg Gly Gly Met Arg); (c) amino acids 38 to 44 of SEQ ID NO: 2 (Ser Arg Gly Gly Met Arg Lys); (d) amino acids 8 and 9 of SEQ ID NO: 2 (Asp Asp); (e); or amino acids 8 and 9 of SEQ ID NO: 3 (Ser Gly). Preferably the domain I β2GP1 polypeptide comprises one of (a), (b) or (c) and one of (d) or (e), such as (b) and (d), or (b) and (e). These amino acids have been shown through mutagenesis studies to be important for binding, either collectively or individually.

In some embodiments, amino acid 40 of SEQ ID NOs: 2 or 3 (Gly) may be changed to Glu. Alternatively or additionally, amino acid 43 of SEQ ID NOs: 2 or 3 (Arg) may be changed to Gly. These alternations do not result in any significant loss of binding (Ioannou Y, et al., *Arthritis and rheumatism* 2007, 56(1):280-290). Preferably the domain I β2GP1 polypeptide does not include a Ser residue at position 39 of SEQ ID NOs: 2 or 3. Preferably, the domain I β2GP1 polypeptide is unmodified from the wild-type sequence of SEQ ID NO: 2 or the D8/D9 variant of SEQ ID NO: 3.

Methods for the preparation and purification of the domain I β2GP1 polypeptide are known in the art such as Ioannou Y. et al., BMC biotechnology 2006, 6:8, and Pericleous C. et al., Molecular Immunology 2011, 49(1-2): 56-63, the contents of which are herein incorporated by reference.

An improved expression system is also disclosed in the Examples described herein, which increased the production yield by ~20 fold compared to previous methods in *E. coli*. After further purification and fusion tag removal, the maximal yield was 50-75 mg per L of expression media. This represents a 20 fold increase on previous *E. coli* expression protocols using in vivo folding by periplasmic localisation (750 μg/L (Ioannou Y et al., *BMC biotechnology* 2006, 6:8) or in vitro folding (~4 mg/L (Pericleous C et al., *Molecular immunology* 2011, 49(1-2):56-6).

In another aspect, the invention provides methods for detection of an anti-β2GP1 antibody, for example an anti-domain I β2GP1 antibody in a sample comprising (a) contacting the sample with a domain I β2GP1 polypeptide conjugate of the Invention under conditions that permit the formation of a stable antigen-antibody complex; and (b) detecting stable complex formed in step (a), if any. The anti β2GP1 antibody may be an IgG, IgM or IgA antibody. Preferably, the anti-β2GP1 antibody is an IgA antibody. The domain I β2GP1 polypeptide conjugate of the Invention render these methods particularly useful, as no generally convenient or suitable assay for these detecting IgA anti-domain I β2GP1 antibodies has yet been developed.

A number of immunoassay methods are well known in the art. Suitable samples in which to measure anti β2GP1 antibody include serum or plasma (preferably serum) and target tissue eluate. It is well understood in the art that detection of a complex formed may be direct (such as by measuring the amount of label associated with a complex) or indirect (such as in measuring the amount of labeled ligand which is displaced during the assay).

To use the domain I β2GP1 polypeptide conjugate of the Invention in the detection of antibodies in an individual, an immunoassay may be conducted. The domain I β2GP1 polypeptide conjugate is provided as a reagent, and the antibody is the target in the biological sample.

For example, human IgG antibody molecules present in a serum sample may be captured with solid-phase protein A, and then overlaid with the labeled domain I β2GP1 polypeptide conjugate reagent. The amount of antibody would then be proportional to the label attached to the solid phase.

Alternatively, in the methods of the invention, domain I β2GP1 polypeptide conjugates of the Invention may be immobilised, by known techniques, onto a suitable solid phase, such as affinity column packing material, or a plastic surface such as a microtiter plate or a dipstick. Appropriate affinity column packing materials include, for example, a beaded agarose matrix, polyacrylamide, glass, cellulose or cross-linked dextran. Suitable plastic surfaces include polymethacrylate, polystyrene, polyethylene, polyterepthalate, ethylene glycol, polyester, polypropylene, and the like. Generally, any standard microtiter plate may be used. Alternatively, the solid phase may be in the form of a gel or matrix into which the domain I β2GP1 polypeptide conjugate is incorporated.

Preferably the domain I β2GP1 polypeptide used in the methods of the invention includes an affinity tag, for example a polyhistidine tag, that either binds to a ligand linked to the solid phase or contains an epitope (such as the FLAG or Myc tags) that is recognised by antibodies immobilised on the solid phase. The high affinity of these tags for their ligands and the availability of well-developed immobilised supports for capturing the fusion proteins are well known in the art. For example, the purification of his-tagged proteins is based on the use of a chelated metal ion as an affinity ligand; one commonly used ion is the immobilised nickel-nitrilotriacetic acid chelate [Ni-NTA], which is bound by the imidazole side chain of histidine. Similarly, Streptag II, which consists of a streptavidin-recognising octapeptide (WSHPQFEK), can be purified by affinity using a matrix with a modified streptavidin and eluted with a biotin analog. Other commonly used affinity tags like FLAG, Myc, and HA can be used to bind to respective antibodies immobilised on solid supports. These affinity tags can be added at either end of the domain I β2GP1 polypeptide or elsewhere in the polypeptide chain.

In some embodiments, a test sample potentially containing an anti-β2GP1 antibody can also be mixed with a pre-determined non-limiting amount of a domain I β2GP1 polypeptide conjugate of the Invention which is generally detectably labeled (such as with a radioisotope or enzyme). In a liquid phase assay, unreacted reagents are removed by a separation technique, such as filtration or chromatography. In these immunoassay techniques, the amount of label associated with the complex positively correlates with the amount of anti-β2GP1 antibody present in the sample. Similar assays can be designed in which anti-β2GP1 antibody in the test sample compete with labeled antibody for binding to a limiting amount of the domain I β2GP1 polypeptide conjugate of the Invention. In such an embodiment, the amount of label negatively correlates with the amount of anti-β2GP1 antibody in the sample.

These methods may be especially useful in those contexts in which a particular individual should be tested and/or monitored for presence and/or amount of anti-β2GP1 antibody. This type of assay may indicate, for example, whether a particular disease (or risk of disease) may be indicated (such as a particular form of thrombosis or clotting disorder).

The domain I β2GP1 polypeptide conjugate of the invention may also be used as a diagnostic component in a coagulation assay (such as the lupus anticoagulant assay), specifically an assay in which anti-β2GP1 antibodies can modify the outcome of a specific coagulation assay. For example, if the presence of a domain I β2GP1 polypeptide conjugate of the Invention alters the outcome of a coagulation assay (when compared to the results of such an assay in the absence of a domain I β2GP1 polypeptide conjugate of the Invention anti-β2GP1 antibodies are implicated in the clotting pathway.

In the conjugates of the invention, the water-soluble polymer is bonded via thiol groups provided by reduction of a disulfide bridge in the domain I β2GP1 polypeptide. Domain I β2GP1 polypeptide contains two disulfide bonds, a first disulfide bond bridging the 1st and 3rd cysteine residues, and a second disulfide bond bridging the 2nd and 4th cysteine residues of the domain I β2GP1 polypeptide sequence. In the native protein sequence shown in SEQ ID NO: 1, the first disulfide bond is between residues 4 and 47, and the second disulfide bond is between residues 32 and 60. Thus, in principle, conjugates according to the invention may contain polymer bonded to the cysteine residues forming either one or two disulfide bonds. Preferably however, the conjugate contains polymer bonded only to the cysteine residues forming a single disulfide bond.

The polymer chain may be linear or branched.

The water-soluble polymer may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally, the polymer may be a polymer that is susceptible to enzymatic or hydrolytic degradation. Such polymers, for example, include polyesters, polyacetals, poly(ortho esters), polycarbonates, poly(imino carbonates), and polyamides, such as poly (amino acids). A polymer may be a homopolymer, random copolymer or a structurally defined copolymer such as a block copolymer, for example it may be a block copolymer derived from two or more alkylene oxides, or from poly (alkylene oxide) and either a polyester, polyacetal, poly (ortho ester), or a poly(amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid), hyaluronic acid and derivatives thereof. A protein may be used as the polymer. Polymers such as polyglutamic acid may also be used, as may hybrid polymers derived from natural monomers such as saccharides or amino acids and synthetic monomers such as ethylene oxide or methacrylic acid.

If the polymer is a polyalkylene glycol, this is preferably one containing $C_2$ and/or $C_3$ units, and is especially a polyethylene glycol. Unless the context requires otherwise, any reference to a polymer throughout this Specification should be understood to include a specific reference to polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted, or capped, polyalkylene glycols, for example methoxypolyethylene glycol, may be used.

The polymer may, for example, be a comb polymer produced by the method described in WO 2004/113394, the contents of which are incorporated herein by reference. For example, the polymer may be a comb polymer having a general formula:

$$A\text{-}(D)_d\text{-}(E)_e\text{-}(F)_f$$

where:

A may or may not be present and is a moiety capable of binding to a protein or a polypeptide;

D, where present, is obtainable by additional polymerisation of one or more olefinically unsaturated monomers which are not as defined in E;

E is obtainable by additional polymerisation of a plurality of monomers which are linear, branched, or star-shaped substituted or non-substituted, and have an olefinically unsaturated moiety;

F, where present, is obtainable by additional polymerisation of one or more olefinically-unsaturated monomers which are not as defined in E;

d and f are an integer between 0 and 500;

e is an integer of 0 to 1000;

wherein when A is present, at least one of D, E and F is present.

Water soluble polymers, particularly water-soluble synthetic polymers, particularly polyalkylene glycols, are widely used to conjugate therapeutically active molecules such as proteins. Water soluble polymers are generally those that are soluble in water or an aqueous medium under ambient conditions of room temperature and atmospheric pressure at a pH of between about 6 and 8, i.e., at about neutral or physiological pH. Preferably, the polymer has a solubility in water, measured at 25° C., of at least about 0.1 gram/liter (g/L), preferably more than 0.3 gram/liter, most preferably more than 0.5 gram/liter. In some embodiments, the polymers have solubility in water, measured at 25° C., of from about 0.1 gram/liter (g/L) to about 500 grams/liter (g/L).

The polymer may optionally be derivatised or functionalised in any desired way. In one preferred embodiment, the polymer carries a diagnostic agent, an additional therapeutic agent, or a labelling agent, or a binding agent capable of binding a diagnostic agent, additional therapeutic agent, or labelling agent. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. Multimeric conjugates that contain more than one biological molecule, can result in synergistic and additive benefits. For example, the conjugate may comprise two or more domain I β2GP1 polypeptides. If desired, the polymer may be coupled to a solid support using conventional methods.

The optimum molecular weight of the polymer will of course depend upon the intended application and duration of the effect that is required. Long-chain polymers may be used, for example the number average molecular weight may be in the range of from 500 g/mole to around 75,000 g/mole. For example the polymer may have a molecular weight of at least 5, 10, 15, 20, 30, or 40 kDa.

The present invention also provides a process for the preparation of a conjugate according to the invention, which comprises reacting domain I β2GP1 polypeptide with a polymer conjugating reagent capable of reacting with the two sulfur atoms present in one of the disulfide bonds in the polypeptide, and thus being capable of binding to said polypeptide via two cysteine residues derived from a disulfide bridge in the polypeptide. Generally, the first step in the reaction will involve reducing the relevant disulfide bond, the two sulfur atoms subsequently reacting with the conjugating reagent.

One suitable group of polymer conjugating reagents are bis-halo- or bis-thio-maleimides and derivatives thereof as described in Smith et al, J. Am. Chem. Soc. 2010, 132, 1960-1965, and Schumaker et al, Bioconj. Chem., 2011, 22, 132-136. These reagents contain the functional grouping:

(VI)

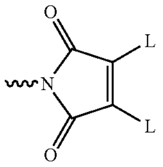

in which each L is a leaving group, for example one of those mentioned below, and in which the nitrogen atom in the formula VI is bonded directly or indirectly to a water-soluble polymer. Typical leaving groups include halogen atoms, for example chlorine, bromine or iodine atoms, —$S.CH_2CH_2OH$ groups, and —S-phenyl groups.

Preferably however the conjugating reagent contains the functional grouping:

(I)

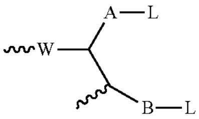

in which W represents an electron-withdrawing group, for example a keto group, an ester group —O—CO—, a sulfone group —$SO_2$—, or a cyano group; A represents a $C_{1-5}$ alkylene or alkenylene chain; B represents a bond or a $C_{1-4}$ alkylene or alkenylene chain; and each L independently represents a leaving group; and in which the functional grouping (I) is bonded directly or indirectly to a water-soluble polymer at one of the points shown. When reagents containing such groups react with proteins, a first leaving group L is lost to form in situ a conjugating reagent containing a functional grouping of formula:

(II)

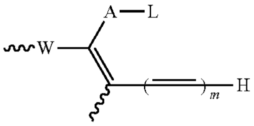

in which m is 0 to 4, which reacts with a first nucleophile. The second leaving group L is then lost, and reaction with a second nucleophile occurs. As an alternative to using a reagent containing the functional grouping I as starting material, reagents containing the functional grouping II may be used as starting material.

Preferably W represents a keto group. Preferably A represents —$CH_2$— and B represents a bond.

Particularly preferred functional groupings of formula I and II have the formulae:

(Ia)

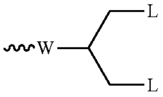

or

-continued (IIa)

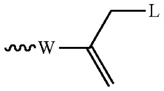

For example, the group may be of the formula:

(Ib)

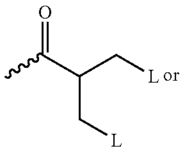

or (IIb)

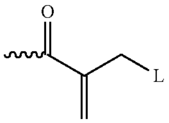

Another group of conjugating reagents contains the functional grouping:

$$\sim W'—CR^1R^{1'}—CR^2.L.L' \quad (III)$$

in which W' has the meaning and the preferred meanings given above, and either $R^1$ represents a hydrogen atom or a $C_{1-4}$alkyl group, $R^{1'}$ represents a hydrogen atom, and each of L and L' independently represents a leaving group; or $R^1$ represents a hydrogen atom or a $C_{1-4}$alkyl group, L represents a leaving group, and $R^{1'}$ and L' together represent a bond; or $R^1$ and L together represent a bond and $R^{1'}$ and L' together represent a bond; and $R^2$ represents a hydrogen atom or a $C_{1-4}$ alkyl group.

Polymer conjugating reagents of the type I, II and III are described in WO 2005/007197 and WO 2010/100430, the contents of which are incorporated herein by reference. Such reagents have the formula I', II' or III' below:

(I')

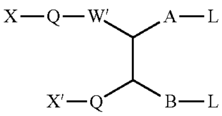

in which one of X and X' represents a polymer and the other represents a hydrogen atom;

Q represents a linking group;

W' represents an electron-withdrawing group, for example a keto group, an ester group —O—CO— or a sulfone group —$SO_2$—; or, if X' represents a polymer, X-Q-W' together may represent an electron withdrawing group;

A represents a $C_{1-5}$ alkylene or alkenylene chain;

B represents a bond or a $C_{1-4}$ alkylene or alkenylene chain; and each L independently represents a leaving group;

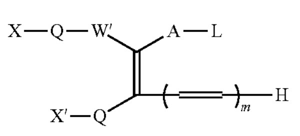

(II')

in which X, X', Q, W', A and L have the meanings given for the general formula I', and in addition if X represents a polymer, X' and electron-withdrawing group W' together with the interjacent atoms may form a ring, and m represents an integer 1 to 4; or $$X\text{-}Q\text{-}W'\text{—}CR^1R^{1'}\text{—}CR^2.L.L' \quad (III')$$

in which X, Q and W' have the meanings given for the general formula I', and either $R^1$ represents a hydrogen atom or a $C_{1-4}$alkyl group, $R^{1'}$ represents a hydrogen atom, and each of L and L' independently represents a leaving group; or $R^1$ represents a hydrogen atom or a $C_{1-4}$alkyl group, L represents a leaving group, and $R^{1'}$ and L' together represent a bond; or $R^1$ and L together represent a bond and $R^{1'}$ and L' together represent a bond; and $R^2$ represents a hydrogen atom or a $C_{1-4}$ alkyl group.

When using these polymer conjugation reagents, conjugates of the invention having the general formulae:

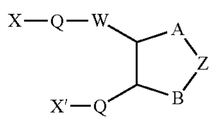

or

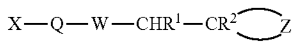

are prepared, where X, Q, X', A, B, $R^1$ and $R^2$ have the meanings and the preferred meanings given herein, W represents an electron withdrawing group or a group preparable by reduction of an electron withdrawing group, and Z represents domain I β2GP1 polypeptide linked to the rest of the molecule via two thiol groups derived from a disulfide bond present in the domain I β2GP1 polypeptide. In one preferred embodiment of such conjugates, X is polyethylene glycol; X'Q- is H; and W is CO or CH.OH; and preferably A and B are both $CH_2$.

A linking group Q may for example be a direct bond, an alkylene group (preferably a $C_{1-10}$ alkylene group), or an optionally-substituted aryl or heteroaryl group, any of which may be terminated or interrupted by one or more oxygen atoms, sulfur atoms, —NR groups (in which R represents a hydrogen atom or an alkyl (preferably $C_{1-6}$alkyl), aryl (preferably phenyl), or alkyl-aryl (preferably $C_{1-6}$alkyl-phenyl) group), keto groups, —O—CO— groups, —CO—O— groups, —O—CO—O, —O—CO—NR—, —NR—CO—O—, —CO—NR— and/or —NR.CO— groups. Such aryl and heteroaryl groups Q form one preferred embodiment of the invention. Suitable aryl groups include phenyl and naphthyl groups, while suitable heteroaryl groups include pyridine, pyrrole, furan, pyran, imidazole, pyrazole, oxazole, pyridazine, primidine and purine. Especially suitable linking groups Q are heteroaryl or, especially, aryl groups, especially phenyl groups, terminated adjacent the polymer X by a —CO.NR— or, especially, an —NR.CO— group. The linkage to the polymer may be by way of a hydrolytically labile bond, or by a non-labile bond.

W' may for example represent a keto group CO, an ester group —O—CO— or a sulfone group —$SO_2$—; or, if X-Q-W'— together represent an electron withdrawing group, this group may for example be a cyano group. Preferably W' represents a keto group.

Preferably X represent a polymer, and X'-Q- represents a hydrogen atom.

Substituents which may be present on an optionally substituted aryl or heteroaryl group include for example one or more of the same or different substituents selected from alkyl (preferably $C_{1-4}$alkyl, especially methyl, optionally substituted by OH or $CO_2H$), —CN, —$NO_2$, —$CO_2R$, —COH, —$CH_2OH$, —COR, —OR, —OCOR, —$OCO_2R$, —SR, —SOR, —$SO_2R$, —NHCOR, —NRCOR, $NHCO_2R$, —NR.$CO_2R$, —NO, —NHOH, —NR.OH, —C═N—NH-COR, —C═N—NR.COR, —$N^+R_3$, —$N^+H_3$, —$N^+HR_2$, —$N^+H_2R$, halogen, for example fluorine or chlorine, —C≡CR, —C═$CR_2$ and —C═CHR, in which each R independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is especially preferred. Preferred substituents include for example CN, $NO_2$, —OR, —OCOR, —SR, —NHCOR, —NR.COR, —NHOH and —NR.COR.

A leaving group L may for example be —SP, —OP, —$SO_2$P, —$OSO_2$P, —$N^+PR^2R^3$, halogen, or —OØ, in which P represents a hydrogen atom or an alkyl (preferably $C_{1-6}$alkyl), aryl (preferably phenyl), or alkyl-aryl (preferably $C_{1-6}$alkyl-phenyl) group, or is a group which includes a portion —$(CH_2CH_2O)_n$— in which n is a number of two or more, and each of $R^2$ and $R^3$ independently represents a hydrogen atom, a $C_{1-4}$alkyl group, or a group P, and Ø represents a substituted aryl, especially phenyl, group, containing at least one electron withdrawing substituent, for example —CN, —$NO_2$, —$CO_2R^a$, —COH, —$CH_2OH$, —$COR^a$, —$OR^a$, —$OCOR^a$, —$OCO_2R^a$, —$SR^a$, —$SOR^a$, —$SO_2R^a$, —NHCO $R^a$, —$NR^a$, $COR^a$, —$NHCO_2R^a$, —$NPCO_2R^a$, —NO, —NHOH, —$NR^a$ OH, —C═N—NHCOR$^a$, —C═N—$NR^a$ $COR^a$, —$N^+R^a_3$, —$N^+HR^a_2$, —$N^+H_2R^a$, halogen, especially chlorine or, especially, fluorine, —C≡$CR^a$,—C═$CR^a_2$ and —C═$CHR^a$, in which each $R^a$ represents a hydrogen atom or an alkyl (preferably $C_{1-6}$alkyl), aryl (preferably phenyl), or alkyl-aryl (preferably $C_{1-6}$alkyl-phenyl) group.

Conjugating reagents in which P represents a group which includes a portion —$(CH_2CH_2O)_n$— in which n is a number of two or more are the subject of our copending UK patent application ref. P022955 GB. This application discloses the following:

"The leaving group may for example include —$(CH_2CH_2O)_n$—$R^1$ where $R^1$ is a capping group. A very wide range of capping groups may be used. $R^1$ may for example be a hydrogen atom, an alkyl group, especially a $C_{1-4}$alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —$CH_2CH_2CO_2H$ or —$CH_2CH_2NH_2$, and may be prepared by functionalising the terminal unit of a —$(CH_2CH_2O)_n$— chain. Alternatively, rather than being terminated by a capping group, the $—(CH_2CH_2O)_n—$ group may have two points of attachment within the conjugating reagent such that chemically the equivalent of two leaving groups are present, capable of reacting with two nucleophiles.

The $—(CH_2CH_2O)_n—$ portion of the leaving group is based on PEG, polyethylene glycol. The PEG may be straight-chain or branched, and it may be derivatised or functionalised in any way. n is a number of 2 or more, for example 2, 3, 4, 5, 6, 7, 8, 9 or 10. For example, n may be from 5 to 9. Alternatively, n may be a number of 10 or more. There is no particular upper limit for n. n may for example be 150 or less, for example 120 or less, for example 100 or less. For example n may be from 2 to 150, for example from 7 to 150, for example from 7 to 120. The PEG portion $—(CH_2CH_2O)_n—$ of a leaving group may for example have a molecular weight of from 1 to 5 kDa; it may for example be 1 kDa, 2 kDa, 3 kDa, 4 kDa or 5 kDa. A leaving group may if desired contain two or more portions $—(CH_2CH_2O)_n—$ separated by one or more spacers.

A leaving group in a conjugating reagent according to the invention is suitably of the formula —SP, —OP, $—SO_2P$, $—OSO_2P$, $—N^+PR^2R^3$, in which P is a group which includes a portion $—(CH_2CH_2O)_n—$ and each of $R^2$ and $R^3$ independently represents a hydrogen atom, a $C_{1-4}$alkyl group, or a group P. Preferably each of $R^2$ and $R^3$ represents a $C_{1-4}$alkyl group, especially a methyl group, or, especially, a hydrogen atom. Alternatively, the conjugating reagent may include a group of formula —S—P—S—; —O—P—O—; $—SO_2—P—SO_2—$; $—OSO_2—P—OSO_2—$; and $—N^+R^2R^3—P—N^+R^2R^3—$. Specific groups of this type include $—S—(CH_2CH_2O)_n—S—$, $—O—(CH_2CH_2O)_n—O—$; $—SO_2—(CH_2CH_2O)_n—SO_2—$; $—OSO_2—(CH_2CH_2O)_n—OSO_2—$; or $—N^+R^2R^3—(CH_2CH_2O)_n—N^+R^2R^3—$. They can also include groups of the type:

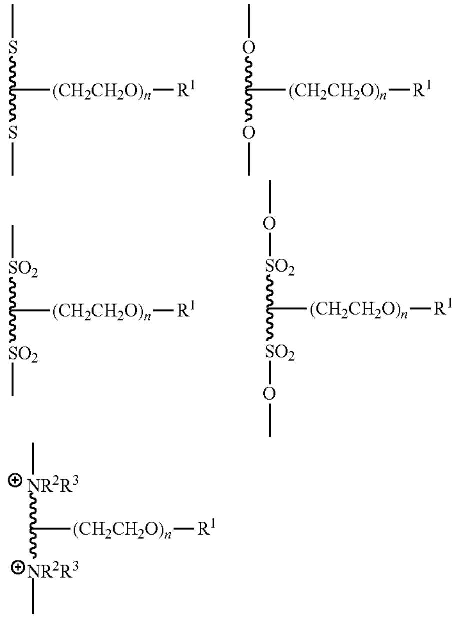

where the $—(CH_2CH_2O)_n—$ group is carried by any suitable linking group, for example an alkyl group. These divalent groups are chemically equivalent to two leaving groups capable of reacting with two nucleophiles."

An especially preferred leaving group L is —SP or $—SO_2P$, especially $—SO_2P$. Within this group, one preferred embodiment is where P represents a phenyl or, especially, a tosyl group. Another preferred embodiment is where P represents a group which includes a portion $—(CH_2CH_2O)_n—$.

An especially preferred polymer conjugation reagent is one of the general formula I which includes the functional group:

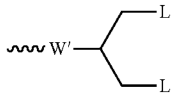

or

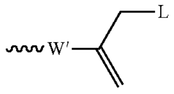

For example, a specific, highly preferred conjugation reagent has the formula:

(Ic)

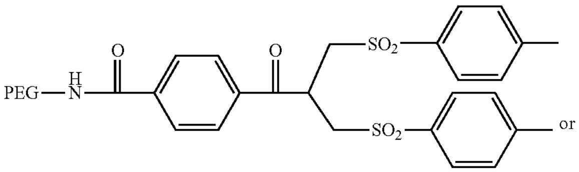

or (IIc)

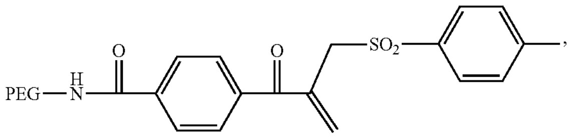

, in which the PEG may optionally carry a diagnostic agent, a therapeutic agent, or a labelling agent, or a binding agent capable of binding a diagnostic agent, a therapeutic agent, or a labelling agent.

The immediate product of the conjugation process using one of the reagents described above is a conjugate which contains an electron-withdrawing group W'. However, the process of the invention is reversible under suitable conditions. This may be desirable for some applications, for example where rapid release of the protein is required, but for other applications, rapid release of the protein may be undesirable. It may therefore be desirable to stabilise the conjugates by reduction of the electron-withdrawing moiety W' to give a moiety which prevents release of the protein. Accordingly, the process may comprise an additional optional step of reducing the electron withdrawing group W' in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Thus, for example, a moiety W' containing a keto group may be reduced to a moiety containing a CH(OH) group; an ether group CH.OR may be obtained by the reaction of a hydroxy group with an etherifying agent; an ester group CH.O.C(O)R may be obtained by the reaction of a hydroxy group with an acylating agent; an amine group $CH.NH_2$, CH.NHR or $CH.NR_2$ may be prepared from a ketone by reductive amination; or an amide CH.NHC(O)R or $CH.N(C(O)R)_2$ may be formed by acylation of an amine. A sulfone may be reduced to a sulfoxide, sulfide or thiol ether. A cyano group may be reduced to an amine group. A key feature of using the conjugation reagents of formulae I, II, III, I', II' or III' described above is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred and bis-alkylation results from sequential and interactive Michael and retro-Michael reactions. The electron withdrawing group and the leaving group are optimally selected so bis-alkylation can occur by sequential Michael and retro-Michael reactions. It is also possible to prepare cross-functional alkylating agents with additional multiple bonds conjugated to the double bond or between the leaving group and the electron withdrawing group.

As mentioned above, the first step in the conjugation reaction will generally involve reducing the relevant disulfide bond, with the two sulfur atoms subsequently reacting with the conjugating reagent in a second step. The process may be carried out as a one-pot process, or in two separate steps. Preferably, the reaction is carried out in an aqueous reaction medium. The solvent may consist of water, or co-solvents may additionally be present.

The first step, reduction of the disulfide bond, may be carried out by known methods, for example using any of the reducing agents known for similar reaction. Generally it is preferred to use a significant excess of reducing agent over stoichiometric, and this may be achieved by the use of relatively high concentrations of reducing agent. For example, the reducing agent may be used at a concentration of at least 20 millimolar, for example from 20 to 150, for example from 80 to 120 millimolar. Preferred reducing agents include tris(2-carboxyethyl)phosphine (TCEP) or, especially, dithiothreitol (DTT). The reduction step is preferably carried out at a temperature in the range of from 10 to 40° C., with room temperature generally being convenient.

The second step, i.e. reaction of the reduced protein with the polymer conjugating reagent, is generally carried out in the presence of a buffer. Unusually for this type of reaction, it has been found that the optimum pH for the reaction is preferably between about 7.0 and about 8.5, preferably about 7.5 to 8.5. The optimal reaction conditions will of course depend upon the specific reactants employed. Surprisingly, it has been found that the presence of arginine in the buffered reaction mixture gives a much improved reaction, possibly by stabilising the protein and reducing aggregation. Preferably the molar ratio of polymer conjugating reagent to arginine is in the range of from 0.5:1 to 3:1, for example from 0.5:1 to 1.5:1, especially from 0.8:1 to 1.2:1. Further, it has been found advantageous to include a chelating agent, for example ethylene diamine tetraacetic acid (EDTA), in the buffered reaction mixture. Preferably the EDTA is present in a concentration of from 20 to 60 millimolar.

The second step of the reaction is generally conducted at a temperature up to ambient temperature. The use of cooling is preferred; for example, the reaction may be carried out at a temperature of from 2 to 10, preferably from 2 to 5° C.

Thus, a preferred process according to the invention comprises reducing a disulfide bond in domain I β2GP1 polypeptide, and reacting the resulting product with a polymer conjugation reagent capable of conjugating with both of the resulting sulfur atoms, especially a reagent as described above and particular a reagent of the formula I, II, III, I', II' or III' described above, in the presence of a buffer at a pH in the range of from 7.0 to 8.5, especially from 7.5 to 8.5, in the presence of arginine, and preferably also in the presence of a chelating agent, especially EDTA, at a temperature in the range of from 2 to 10° C.

The domain I β2GP1 polypeptide can be effectively conjugated with the desired reagent using a stoichiometric equivalent or an excess of polymer conjugating reagent. Excess reagent and the product can be easily separated during routine purification, for example by standard chromatography methods, e.g. ion exchange chromatography or size exclusion chromatography, diafiltration, or, when a polyhistidine tag is present, by separation using metal affinity chromatography, e.g. based on nickel or zinc.

Conjugates of the invention are expected to display favourable pharmacokinetics due to prolonged circulation time and decreased clearance rate. The remarkable finding that such conjugates retain the ability to inhibit binding of anti-β2GPI antibodies to β2GPI at levels at least as efficacious as those shown by the unconjugated protein makes the conjugates particularly suitable for use in therapy, specifically for the treatment or prevention of APS or seronegative APS (SNAPS). In particular, the conjugates of the invention may be used for treating clots (thrombosis), pregnancy-related complications such as miscarriage, stillbirth, preterm delivery, and preeclampsia in patients with APS or SNAPS. The present invention therefore also provides a method of treating, preventing or alleviating APS or SNAPS which comprises the administration to a patient, especially a human patient, of a conjugate according to the invention. The conjugate can be administered to the patient prior to, simultaneously with, or after administration of another active agent, for example another agent having activity against APS or SNAPS such as an anticoagulant. The invention therefore further provides a pharmaceutical composition comprising a conjugate according to the invention together with a pharmaceutically acceptable carrier, optionally together with an additional active agent.

BRIEF DESCRIPTION OF THE DRAWINGS

The invention will now be described by way of example with reference to the drawings, in which:—

Figure 4A:
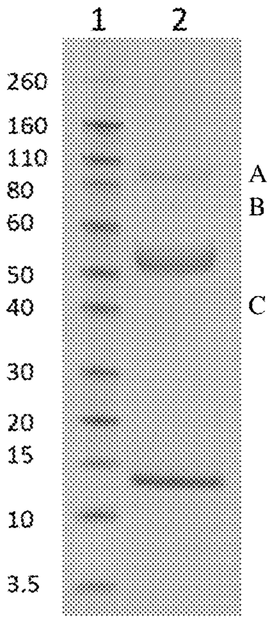
FIG. 4A is an SDS-PAGE gel showing crude pegylation reaction mixture of Wild-type DI-20 kDa PEG conjugate.
Figure 4B:
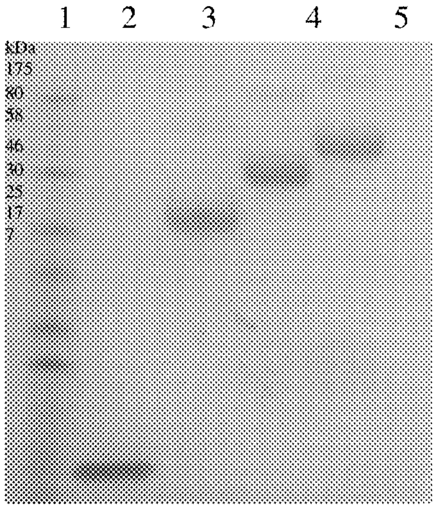
Figure 5A:
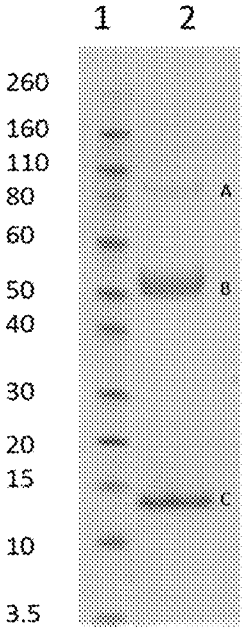
Figure 5B:
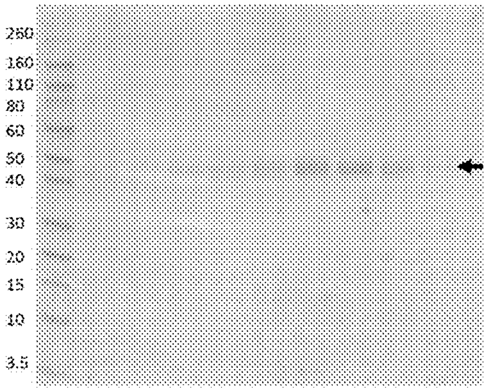
Figure 6A:
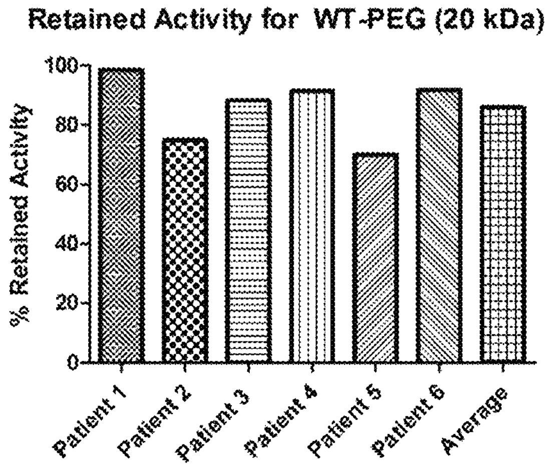
Figure 6B:
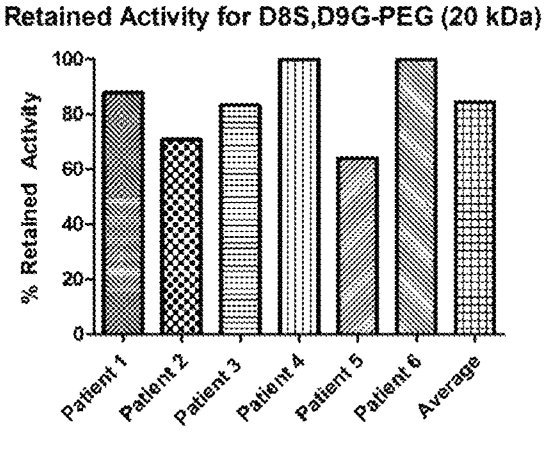
Figure 7A:
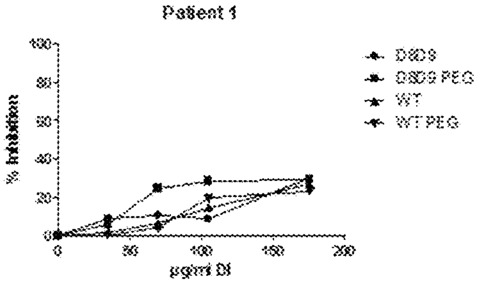
Figure 7B:
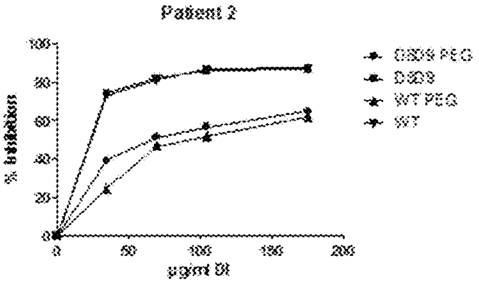
Figure 7C:
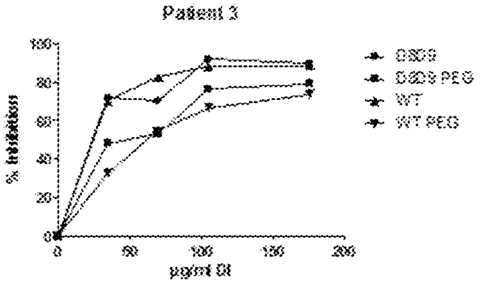
Figure 7D:
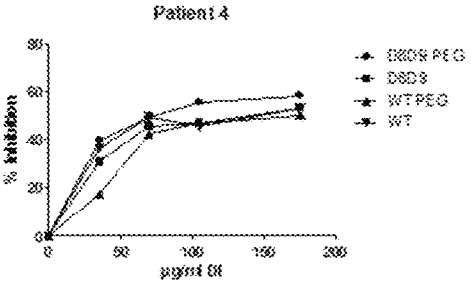
Figure 7E:
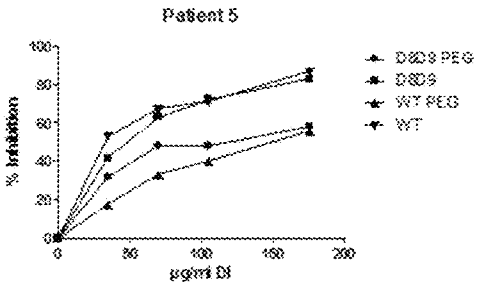
Figure 7F:
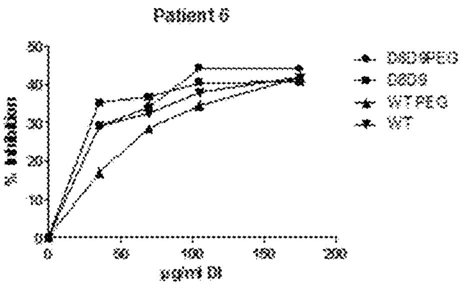
Figure 8A:
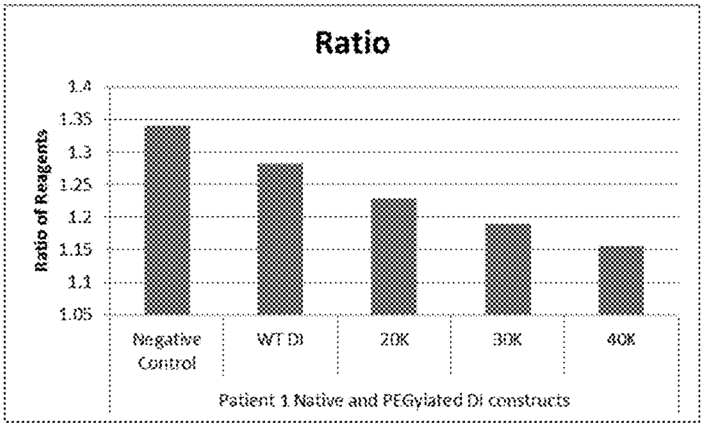
Figure 8B:
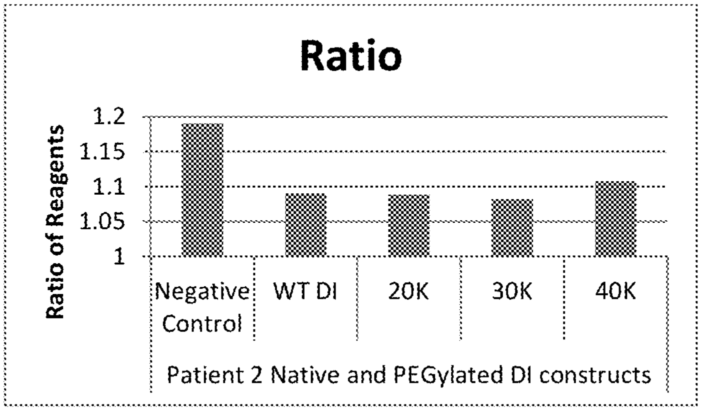
Figure 8C:
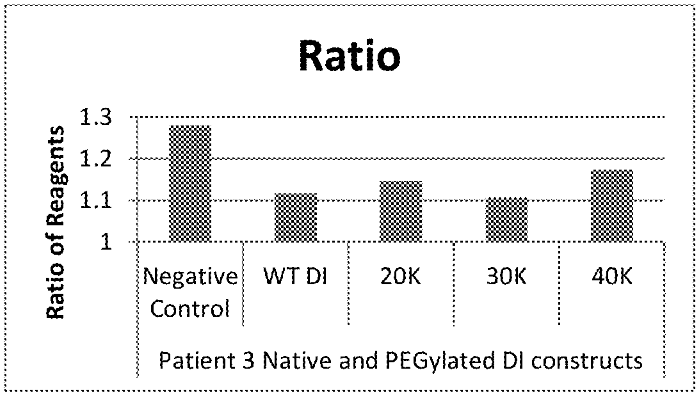
Figure 8D:
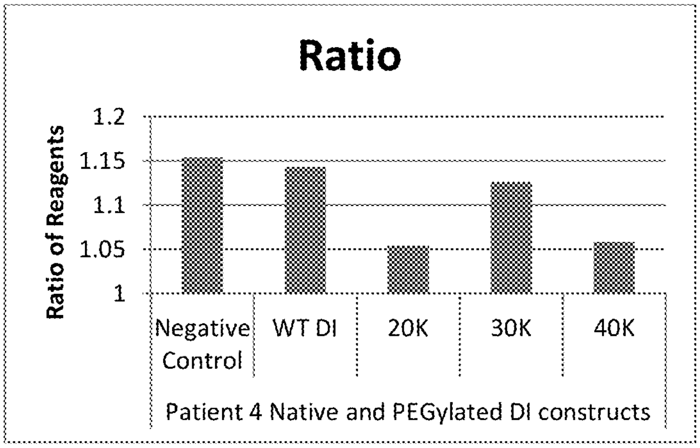
Figure 9:
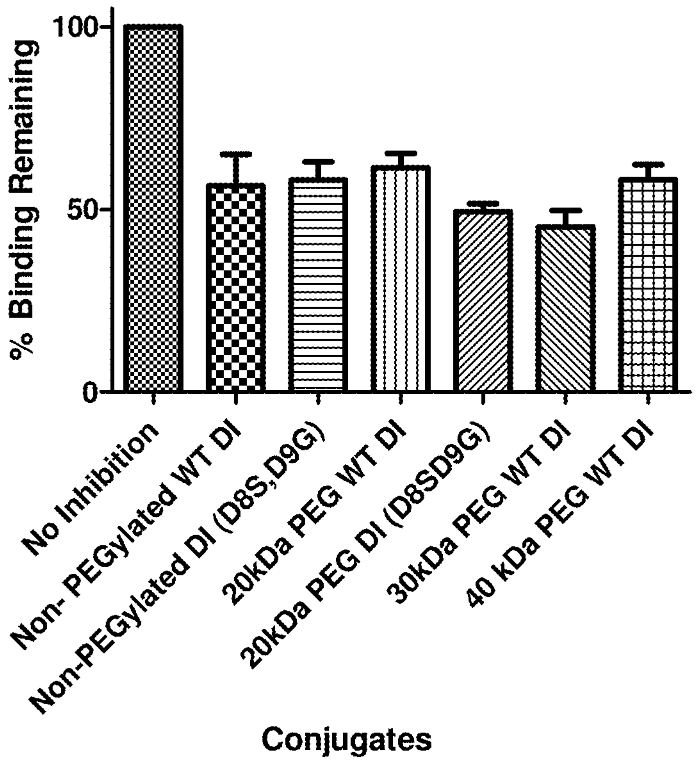
Figure 10:
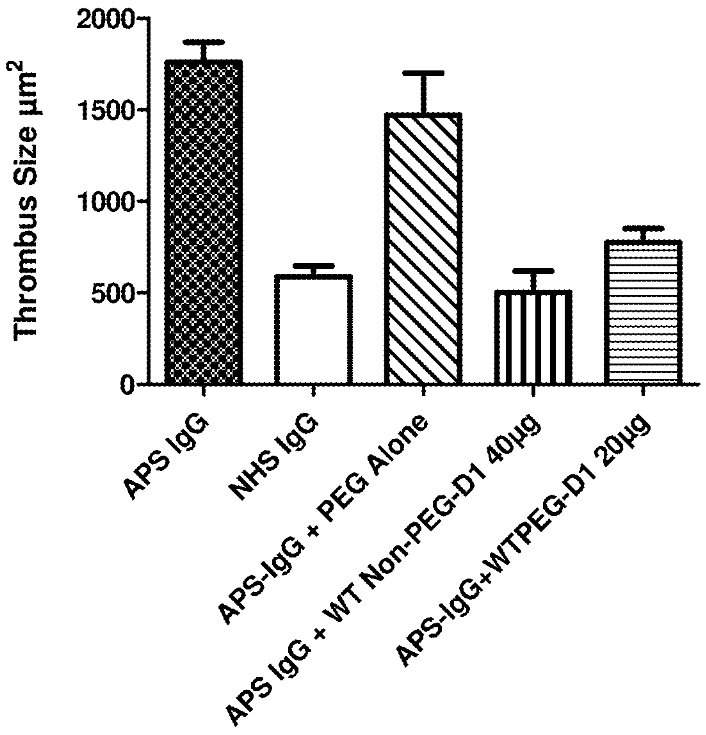

Lane 1, Mr weight markers as indicated. Lane 2, A—Di-pegylated Wt DI-20 kDa PEG conjugate; B—Mono-pegylated Wt DI-20 kDa PEG conjugate; C—Unconjugated Wt DI protein [Wt DI is the wild-type domain I sequence of SEQ ID NO: 2];

FIG. 4B is an SDS-PAGE gel showing purified pegylated Wild-type DI protein conjugates. Lane 1—Mr weight markers as indicated, Lane 2—unconjugated Wild-type DI (approximately 7 kDa), Lane 3—Pegylated Wt-DI (20 kDa PEG), Lane 4—Pegylated Wt-DI (30 kDa PEG), Lane 5—Pegylated Wt-DI (40 kDa PEG);

FIG. 5A is an SDS-PAGE gel showing crude pegylation reaction mixture of the non-cleaved D8S,D9G mutant DI-20 kDa PEG conjugate. Lane 1, Mr weight markers as indicated. Lane 2, A—Di-pegylated D8S,D9G mutant DI-20 kDa PEG conjugate; B—Mono-pegylated D8S,D9G mutant DI-20 kDa PEG conjugate; C—Unconjugated D8S,D9G mutant DI protein [D8S,D9G mutant DI is a variant domain I sequence of SEQ ID NO: 3];

FIG. 5B is an SDS-PAGE gel showing purified cleaved pegylated D8S,D9G mutant DI protein. Lane 1—Mr weight markers as indicated, Lanes 2-10—Pegylated D8S,D9G mutant DI protein;

FIG. 6A shows the results of a competitive inhibition ELISA. The graph shows retained inhibitory activity of pegylated-WT (wild-type) as a % of its non-pegylated counterpart;

FIG. 6B shows the results of a competitive inhibition ELISA. Graph shows retained inhibitory activity of pegylated-DI(D8S,D9G) variant protein as a % of its non-pegylated counterpart;

FIG. 7A shows the results of competitive inhibition ELISA data showing % inhibition concentration response curves for Patient 1;

FIG. 7B shows the results of competitive inhibition ELISA data showing % inhibition concentration response curves for Patient 2;

FIG. 7C shows the results of competitive inhibition ELISA data showing % inhibition concentration response curves for Patient 3;

FIG. 7D shows the results of competitive inhibition ELISA data showing % inhibition concentration response curves for Patient 4;

FIG. 7E shows the results of competitive inhibition ELISA data showing % inhibition concentration response curves for Patient 5;

FIG. 7F shows the results of competitive inhibition ELISA data showing % inhibition concentration response curves for Patient 6;

FIG. 8A shows the results of a coagulometer assay data showing ratios of clotting times in blood plasma samples, with purified Patient 1 IgG, treated with either wild-type domain I (WT) or pegylated variants of wild-type domain I (with different molecular weights PEGs: 20 kDa, 30 kDa and 40 kDa;

FIG. 8B shows the results of a coagulometer assay data showing ratios of clotting times in blood plasma samples, with purified patient 2 IgG, treated with either wild-type domain I (WT) or pegylated variants of wild-type domain I (with different molecular weights PEGs: 20 kDa, 30 kDa and 40 kDa);

FIG. 8C shows the results of a coagulometer assay data showing ratios of clotting times in blood plasma samples, with purified patient 3 IgG, treated with either wild-type domain I (WT) or pegylated variants of wild-type domain I (with different molecular weights PEGs: 20 kDa, 30 kDa and 40 kDa);

FIG. 8D shows the results of a coagulometer assay data showing ratios of clotting times in blood plasma samples, with purified patient 4 IgG, treated with either wild-type domain I (WT) or pegylated variants of wild-type domain I (with different molecular weights PEGs: 20 kDa, 30 kDa and 40 kDa);

FIG. 9 shows the results of Example 8, and illustrates the inhibition of IgA binding to immobilised β2GP1 by PEGylated and non-PEGylated wild-type and mutant (D8SD9G) D1 constructs;

FIG. 10 shows the results of Example 9, and illustrates the inhibitory effects of PEGylated and non-PEGylated wild-type D1 in a mouse blood clot model.

EXAMPLES

All chemicals were purchased from Sigma, unless otherwise stated.

Example 1

DI Expression Vector Construction

Figures 1A, 1B:
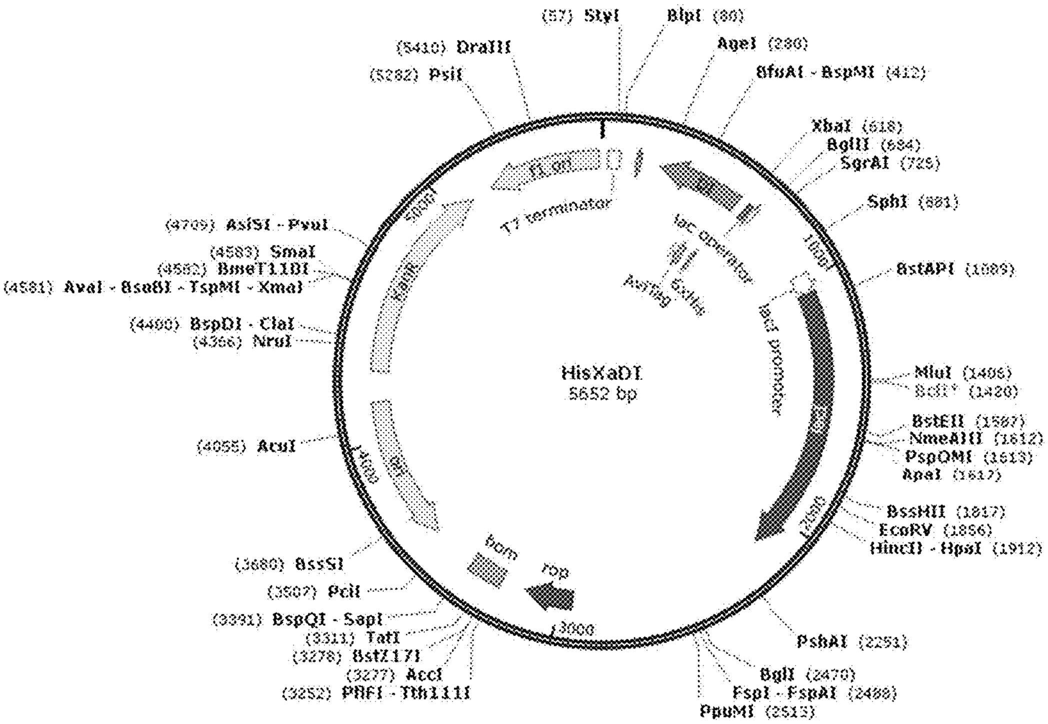
FIG. 1A shows a DI fusion protein sequence showing the N-terminal hexa-histidine tag (italics), the BirA recognition site for potential biotinylation (boxed) and the restriction protease Fxa cleavage site (underlined). The cleavage site is indicated with an arrow and the first amino acid of Domain I (M) is bolded.
FIG. 1B is a map of expression vector containing HisXaDI construct. DI sequence location is indicated.

The synthetic DI coding sequence as previously published (Ioannou Y, et al., BMC biotechnology 2006, 6:8) was cloned into a modified vector that incorporates an N-terminal fusion tag consisting of an hexa-histidine motif, a BirA biotinylation site and a Factor Xa recognition sequence for proteolytic cleavage (FIG. 1A) and vector map (FIG. 1B). These modifications were introduced into the vector pETHis_1a, which is itself a modified pET24d vector (Merck Millipore).

Example 2

Small and Large Scale Protein Expression Test in Lysogeny Broth (LB) and Terrific Broth (TB)

Transformation of BL21*DE3® (Life Technologies) cells was carried out according to the manufacturer's instructions, cells were plated into LB/agar with kanamycin 50 μg/ml. Single colonies were picked and subcultured into 3 ml of LB media containing kanamycin (50 μg/ml) and incubated overnight at 250 rpm and 37° C.

150 μl of preculture were used to inoculate 3 ml of LB or TB and cells were incubated at 250 rpm and 37° C.; growth was monitored by OD at 600 nm.

In order to optimise the conditions for the protein expression preliminary small scale expression tests were performed in 24-well plate format. The following conditions were tested: Type of medium (LB or TB), IPTG concentration (0.5 mM, 1 mM or 2 mM), length of incubation after induction (8 or 16 hours) and temperature of incubation after induction (20° C. or 37° C.) and optical density ($OD_{600}$) of induction (0.6 LB, or 5-7 TB).

Expression was carried out overnight with shaking at 250 rpm at 20° C. Cells were harvested by centrifugation for 20 minutes at 20,000×g and 4° C. Pellets were lysed in 500 μl of 1% Triton X-100 and 1×PBS, by three cycles of sonication (output 100, 3 minutes) and the crude extract was analysed by SDS-PAGE in order to assess the level of protein expression. Two to three μg of protein were loaded into each well of a 4-12% gradient Bis-Tris Novex®NuPAGE® (Life Technologies). The gel was then washed briefly in ddH2O and stained for 1 hour with InstantBlue™ stain (Expedeon, UK) (FIG. 2).

Large Scale Protein Expression in TB

A glycerol stock was used to inoculate 200 ml of LB. Cultures were incubated overnight with shaking at 225 rpm and 37° C., centrifuged at 3500×G for 30 minutes at room temperature and resuspended in 20 ml of fresh LB. Two liters of TB was seeded in 4 2 L-flasks with 5 ml of pre-culture in each.

Figure 2:
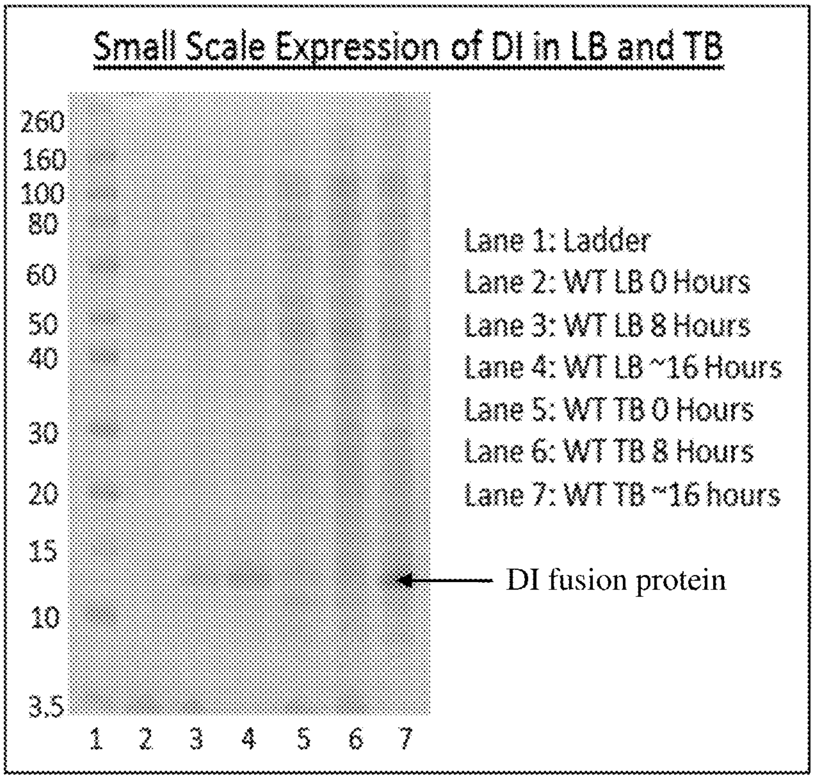
FIG. 2 is an SDS-PAGE gel comparing crude lysates of small scale expression of tagged Domain I fusion protein in LB and TB media before and after induction. Recombinant tagged Domain I fusion is indicated by an arrow and migrates at 12 kDa. Sample concentration was estimated by absorbance at 280 nm measured with a NanoDrop 1000 Spectrophotometer.

Growth in TB with induction at an $OD_{600}$ between 5 and 7 with 1 mM IPTG for 16 hours with shaking at 225 rpm at 20° C. was selected as the best condition for the expression of DI fusion protein (FIG. 2). No changes in expression level were observed when the production was scaled up to 2 liters. Using precultures with an $OD_{600\ nm}$ between 0.1 and 0.2, the expression would reach induction density ($OD_{600}$ nm 5-7) within 5 hours and reach an overnight $OD_{600}$ of approximately 10-13.

Harvesting

Harvesting was carried out using a 500 kDa Hollow Fiber Ultrafiltration Cartridge (GE Healthcare). The cell suspension was run into the cartridge at 100 rpm until a pellet formed, the bacterial pellet was further rinsed by addition of 2 L of PBS. The pellet was transferred into 50 ml centrifuge tubes, spun at 3,500×g for 30 minutes to remove any remaining PBS and finally snap frozen using dry ice.

Bacteria were harvested by either centrifugation (small scale expression) or hollow fiber ultrafiltration (large scale expression). For convenience and suitability for scaling up, ultrafiltration was selected for large scale productions. Typical expression yields were in the order of 20 g of wet cell pellet per liter of culture.

Cell Lysis and Inclusion Body Solubilisation

Lysis Buffer A (50 mM sodium phosphate, 0.3M Sodium Chloride, 10 mM Imidazole) was added to the frozen pellet with the addition of DNase (0.02 mg/ml) and protease inhibitors (1:500). Bacterial pellets were suspended by vortexing and pipette mixing. The lysate was then sonicated (50% intensity, 50% cycles) for 4 minutes, allowed to cool for 2 minutes. This step was repeated once more. The inclusion bodies were collected by centrifugation of the lysate at 3,500×g for 30 minutes. Lighter inclusion bodies were harvested by spinning the supernatant once again at 20,000×g for 30 minutes.

Optimal lysis of the bacterial pellet was achieved using 80 to 100 mL of Buffer A per 40 g of wet cell pellet. Addition of DNase and proteases inhibitors in the lysis buffer led to a marked decrease in viscosity of the lysate and an increase in solubility of inclusion bodies at the solubilisation step. The inclusion bodies were collected by centrifugation, resuspended in Buffer B and homogenised by a combination of grinding with a pestle and mortar, sonicating and pipette mixing; sonication was essential for solubilisation of the inclusion bodies containing DI fusion protein while the incubation temperature had no impact on the solubilisation efficiency. Although using more Buffer B had no impact on the solubilisation yield, less concentrated preparations were less viscous, facilitating subsequent procedures.

Inclusion Body Preparation

The inclusion bodies were resuspended in Solubilisation Buffer B (6 M guanidine hydrochloride, 0.1 M $NaH_2PO_4$, 10 mM Tris, pH 8.0) using a initially by grinding in a pestle and mortar homogeniser. The suspension was sonicated twice for 4 minutes (50% intensity, 50% cycles), in order to promote protein solubilisation and reduce viscosity. The suspension was finally centrifuged at 20,000×g for 20 minutes to remove insoluble debris prior to purification.

Example 3

Purification of Denatured Protein by Immobilised Metal Affinity Chromatography (IMAC)

Solubilised protein from the inclusion bodies was purified by IMAC. The solubilised protein was loaded at 2-5 ml/min onto a 15-ml HisTrap FF (GE Healthcare) and washed with 1.5 column volumes (CV) of Denaturing IMAC Equilibration Buffer C (6 M guanidine hydrochloride, 0.1 M $NaH_2PO_4$, 10 mM Tris, pH 6.3). The protein was eluted at 1 ml/min with 2.7 CV of Denaturing IMAC Elution Buffer D (6 M guanidine hydrochloride, 0.1 M $NaH_2PO_4$, 10 mM Tris, pH 4.5). The fractions were collected and analysed by SDS-PAGE, the entire purification process was conducted on an AKTA platform (GE Healthcare).

Figure 3:
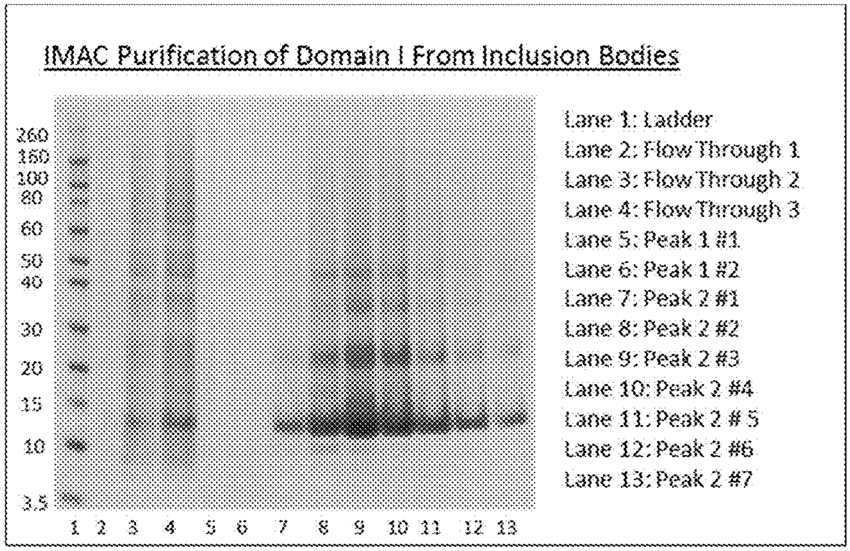
FIG. 3 is an SDS-PAGE gel showing elution profile from IMAC column chromatography under denaturing conditions.

DI fusion protein was eluted with a stepwise pH gradient (8 to 6.3 to 4.5) and elution fractions were analysed by SDS-PAGE (FIG. 3). The flow-through still contained a limited amount of DI fusion protein (Lanes 2-4). Elution fractions showed a high concentration of DI fusion protein at ~12 kDa as well as dimers (~24 kDa) and multimers. In addition, a smaller species (~10 kDa) was observed in the highly concentrated fractions (lanes 8-9) and could correspond to a truncated or a degraded fragment of the fusion protein containing the N-terminal fusion tag.

Following IMAC, the yield of purified denatured DI fusion protein was around 125-150 mg of protein/liter of medium when quantified in guanidine.

Example 4

In Vitro Oxidative Protein Folding

The protein was pooled and concentrated to 25-30 mg/ml by centrifugal concentrators. Any potential disulphide bonds were reduced by incubating overnight with 50 mM TCEP at 4° C. TCEP was subsequently removed by buffer exchange using a PD-10 desalting column (GE Healthcare). The protein was recovered at a concentration of >10 mg/ml and was loaded into a 5 ml syringe. This syringe was fitted into a pump with the tip placed inside 95 mL of the Folding Buffer E (0.6 M arginine hydrochloride, 0.1 M Tris, pH 8.5, 1 mL cysteine (0.3 M)+1 mL cystine (0.03M). The pump was set to inject constantly at 300 μl/hour and left overnight at 4° C. The resulting solution was centrifuged at 3,500×g for 30 minutes at 4° C., syringe filtered (25 μm, Sartorius). The protein solution was further concentrated to approximately 3-5 mg/ml by Vivaspin® centrifugal ultrafiltration (5 kDa MWCO, Satorius) and dialysed for 2 hours (3.5 KDa MWCO, snake skin, thermo scientific) against 5 L of Native IMAC Equilibration Buffer F (20 mM Tris, 0.1 M NaCl, pH 8.0) at 4° C. Dialysis buffer was changed after 2 hours and the protein was further dialysed overnight at 4° C. The resultant protein was collected and used for purification by IMAC.

The maximum yield of soluble protein obtained by continuous addition was 150 mg in 100 ml of Buffer E. Denatured protein concentration during folding was critical for the final yield of soluble protein, protein folded at concentrations lower than 10 mg/mL aggregated overnight.

The soluble DI fusion protein was then concentrated and dialysed against Buffer F prior to IMAC in native conditions. Avoiding high protein concentrations at this stage was critical and a concentration for folded fusion protein of 2 to 2.5 fold was found to be optimal.

Purification of Folded and Monomeric Protein by IMAC in Native Conditions

Dialysed protein was purified using a 15-ml HisTrap FF (GE Healthcare) at a flow rate of 2 ml/min. The flow-through was collected and the column washed with 3-4 CV of Buffer F. The protein was eluted with a gradient 0-100% Native IMAC Elution Buffer G (20 mM Tris, 0.1 M NaCl, 1 M imidazole, pH 8.0) over 8 CV (2 ml/min). Five milliliter fractions were collected and analysed by SDS PAGE. The fractions containing recombinant tagged DI were pooled and stored at 4° C.

IMAC purification at this stage was very successful for the removal of impurities, misfolded species and aggregates. Yield after IMAC purification was between 50-75 mg per liter of expression medium.

Example 5

PEGylation of Expressed, Recombinant Wild Type DI or Mutant (D8S, D9G) DI

Example 5a (Wild Type DI)

Reduction of DI Protein

Prior to PEGylation, purified, recombinant, tagged wild-type DI was dialysed against PBS (30 ml in 2 L of PBS for 2 hours at 4° C. then the buffer was exchanged for 2 L of fresh PBS) and freeze-dried over 48 hours in 1 or 2 mg aliquots.

Freeze-dried Wt DI protein was resuspended in reduction buffer H (2 M arginine, 0.1 M NaCl, 20 mM sodium phosphate, 40 mM EDTA, pH 8.2), to a concentration of 0.44 mg/ml (2 mg in 4.5 ml of reduction buffer H) and left standing at room temperature for 15 minutes to ensure all lyophilised protein was in solution. Sample was mixed by pipetting before addition of 0.5 ml of 1M DTT to the reduction buffer. After DTT was added, sample was mixed thoroughly by pippetting and incubated for 1 hour at 20° C. During this incubation period, 2×2.5 ml PD-10 columns (2.5 ml column volume) were each equilibrated with 20-25 ml of PEGylation buffer I (25 mM arginine, 0.1M NaCl, 20 mM sodium phosphate, 40 mM EDTA, pH 8.2) at room temperature. Following 1 hour reduction, 2.5 ml of DI in reduction buffer H (per PD-10 column) was buffer exchanged to remove DTT and excess arginine (as per manufacturer's instructions). The reduced protein was eluted with 3.5 ml of PEGylation buffer I and the eluate collected into 13 ml PEGylation buffer I at an angle of approximately 60-80° to prevent aggregation when the protein mixes with the solution. This process was repeated with the second 2.5 ml aliquot of reduced DI protein with the second column and the eluate collected into the same tube, giving a final volume of 20 ml (0.1 mg/ml DI protein).

PEGylation of DI Protein 3 mg of (α-methoxy-ω-4-[2,2-bis [(p-tolylsulfonyl)-methyl]acetyl]benzamide poly(ethylene glycol) pegylation reagent 1 (20,000 g/mol):

(1)

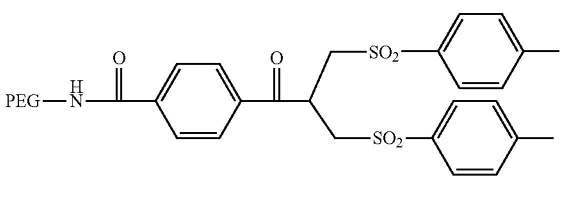

was weighed out into a 1.5 ml eppendorf and resuspended in 150 μl PEGylation buffer I (i.e. 20 mg/ml). PEGylation was carried out by addition of PEG reagent 1 at a 1:1 molar ratio to the DI protein (for 20 kDa PEG-reagent this was 150 μl at 20 mg/ml), and incubated at 4° C. for 4 hours.

Buffer exchange using a HiPrep 26/10 large desalting column was carried out to stop the reaction. A large desalting column (53 ml bed volume) was attached to an AKTA purifier and equibrilated in post-PEGylation purification buffer K (20 mM Sodium Acetate, 0.01% tween 80, pH 6.5), by washing with 100 ml at a flow rate of 5 ml/min. Protein was injected in 2×10 ml volumes at a rate of 5 ml/min and eluted by washing with buffer K at a rate of 5 ml/min, 10 ml fractions were collected containing protein. Each fraction was ended when either the conductivity increased to above 3 mS or UV (Abs 280 nm) levels returned to base level. Fractions were pooled and purified as stated below. FIG. 4A shows the SDS-PAGE gel of the crude PEGylated protein, in which Lane 1, Mr weight markers as indicated. Lane 2, A—Di-PEGylated Wt DI-20 kDa PEG conjugate; B—Mono-PEGylated Wt DI-20 kDa PEG conjugate; C—Unconjugated Wt DI protein.

The experiment was then repeated using for 30 kDa and 40 kDa PEG-reagents, the volumes added being 230 μl and 310 μl at 20 mg/ml, respectively.

Ion Exchange Purification of PEGylated Protein

The AKTA Prime was cleaned with 0.2M NaOH to remove contaminants while the superloop was rinsed 3 times in $ddH_2O$. The buffer exchanged sample was loaded into the superloop and the 5 ml SP HP column attached to the AKTA Prime and washed initially with 3-5 CV of Post-PEGylation Buffer L then equilibrated in 3-5 CV of post-PEGylation Buffer K. Protein was eluted using a linear gradient of Buffer K to Buffer L (20 mM Sodium Acetate, 1M NaCl, 0.01% Tween 80) (up to 50% L).

The SDS-PAGE gel of the purified conjugates is shown in FIG. 4B, in which Lane 1—Mr weight markers as indicated, Lane 2—unconjugated Wild-type DI (approximately 7 kDa), Lane 3—PEGylated Wt-DI (20 kDa PEG), Lane 4—PEGylated Wt-DI (30 kDa PEG), Lane 5—PEGylated Wt-DI (40 kDa PEG).

Dialysis Post-purification and Cleavage of Fusion Protein Tag

Mono-PEGylated protein was dialysed into Post-PEGylation Cleavage Buffer M (50 mM Tris, 0.1 M NaCl, 1 mM $CaCl_2$, pH 6.5). After overnight dialysis, the protein was concentrated to approximately 12 ml, quantified by UV A280 analysis, and FXa enzyme (Haematologic Technologies) added in a 1:100 ratio and the mixture incubated without shaking for ~16 hours at 22° C. Samples were analysed by SDS-PAGE to assess the completion of cleavage.

Post Cleavage Purification

Approximately 0.5 ml of Nickel Resin was loaded into an empty column per 1 mg of sample to be applied. This was then equibrilated with 10 column volumes of post-PEGylation cleavage buffer M. The protein to be purified was then applied to the resin 1 ml at a time and the flow through collected. The sample was then washed through with approximately 10 column volumes of post-PEGylation cleavage buffer M. The flow through and wash were pooled and concentrated to 2 ml using a 10,000 Da MWCO centrifugal concentrator. Meanwhile the SEC was equilibrated in PBS for use. The protein was injected to the column and the fraction collector set at 2 ml fractions. The single peak was pooled and analysed by SDS PAGE for identity and RP-HPLC for purity.

Analysis of Purity by Reverse Phase HPLC

Both VariTide RPC (Agilent) and Poroshell C8 (Agilent) columns were used for RP-HLPC. Ten µg samples were injected and run across either a 4 or a 10 minute gradient of 0-100% solvent B. Solvent A was 2% acetonitrile and 0.065% TFA in $ddH_2O$ and solvent B was 100% acetonitrile and 0.05% TFA. Spectra were analysed using Chromeleon® software (Dionex).

Endotoxin Removal and Quantification

EndoTrap® high capacity columns (Hyglos) were used for endotoxin removal following the manufacturer's instructions with the following adaptations: protein was dialysed to PBS overnight before being dialysed into endotoxin-free PBS via centrifugal ultrafiltration. The buffer was supplemented with 1 mM calcium chloride.

The EndoLISA® fluorescence assay (Hyglos) was used for endotoxin quantification following the instructions of the manufacturer. Presence of endotoxins was tested in proteins samples at concentrations between 2 mg/ml and 0.1 mg/ml.

Example 5b

Mutant (D8S, D9G) DI

The same process as described in Example 5a above was carried out using D8S,D9G mutant DI protein with the following differences: in the reduction step the protein was eluted with buffer J (100 mM arginine, 0.1M NaCl, 20 mM sodium phosphate, 40 mM EDTA, pH 8.2) prior to PEGylation; and PEGylation buffer J was also used in the PEGylation step. The results are shown in FIGS. 5A and 5B, in which FIG. 5A is an SDS-PAGE gel showing crude PEGylation reaction mixture of the non-cleaved D8S,D9G mutant DI-20 kDa PEG conjugate: Lane 1, Mr weight markers as indicated. Lane 2, A—Di-PEGylated D8S,D9G mutant DI-20 kDa PEG conjugate; B—mono-PEGylated D8S,D9G mutant DI-20 kDa PEG conjugate; C—unconjugated D8S, D9G mutant DI protein. FIG. 5B is an SDS-PAGE gel showing SEC elution profile of purified cleaved PEGylated D8S,D9G mutant DI protein stained with iodine and barium chloride to show PEGylated protein: Lane 1—Mr weight markers as indicated, Lanes 2-10 arrow indicates presence of PEGylated D8S,D9G mutant DI protein.

Example 6

Competitive Inhibition ELISA

Competitive inhibition ELISA was carried out to test the ability of recombinant DI to inhibit binding of purified IgG from patients with APS to immobilised β2GPI. The assay was adapted from the standard β2GPI ELISA published by Ioannou et al., (*BMC biotechnology* 2006, 6:8) with the following amendments: the inhibitors were pre-incubated at concentrations ranging from 0 mg/ml to 200 µg/ml rather than 0 to 30 µM. Briefly, the test was carried out to test the ability of recombinant DI to inhibit binding of purified IgG from patients with APS to β2GPI coated on a plate. Recombinant DI was pre-incubated with patient serum prior to addition on the ELISA plate coated with β2GPI. Bound patient IgG was detected with an anti-human IgG HRP secondary antibody. Each sample was tested in duplicate.

Inhibition Retained Activities:

TABLE 1

Retained activity indicated for 175 ug/ml test protein (DI, DI-PEG, D8S, D9G or D8S, D9G-PEG). See FIGS. 6A and 6B for graphical representation of these data.

| Patient Number | Retained Activity of WT DI-PEG (20 kDa) Vs WT DI (%) (175 µg/ml of test protein) | Retained Activity of D8S, D9G mutant-PEG (20 kDa) Vs D8S, D9G (%) (175 µg/ml of test protein) |
|---|---|---|
| 1 | 98.5 | 87.8 |
| 2 | 74.9 | 70.8 |
| 3 | 88.3 | 83.3 |
| 4 | 91.5 | 100 |
| 5 | 70 | 64 |
| 6 | 91.9 | 100 |

Competitive inhibition data is generally expressed as retained binding of the antibody to the antigen on the plate in the presence of the inhibitor protein (DI-PEG or DI). These data can be converted to % inhibition by calculating the inverse of the % binding remaining. Activities of PEGylated or non-PEGylated DI are given based on % inhibition. FIGS. 7A-7F show % inhibition data for pegylated and non-pegylated DI constructs.

Regarding the activity of the protein, the inter patient variability in susceptibility to inhibition by DI is likely due to the fact that some patients possess anti-β2GPI antibodies that interact with other domains (DII-V) and is entirely consistent with results from previous experiments using DI expressed in insect cells (Iverson G M, et al., *Proceedings of the National Academy of Sciences of the United States of America* 1998, 95(26):15542-15546).

Example 7

Coagulometer Assays

LA (Lupus Anticoagulant) Dilute Russel Viper Venom (dRVT-plus) Assay:

Assay reagents were used as described in manufacturer's (Haematex) instructions.

This assay reproduces the "lupus anticoagulant" (LA) effect, a test in which antibodies from serum of patients with APS cause a measurable prolongation of clotting time under specific conditions in vitro. Purified IgG from four patients with APS (shown as FIGS. 8A-8D) was pre-incubated with the DI constructs at a molar ratio of ~1:1 (500 µg/ml antibody and 25 µg/ml DI) before being added to normal human plasma either with or without excess phospholipid—which prevents the anticoagulant effect of the IgG. The results are expressed as ratio of clotting time in absence to that in the presence of excess phospholipid. The higher the ratio, the greater the biological effect exerted by the IgG-APS. The bar for the negative control denotes the result (i.e., the ratio) obtained in the absence of DI and the bar for the wild-type domain I (WT DI) shows the effect of non-PEGylated DI. It is clear that PEGylated DI at a range of PEG sizes retains the ability of the wild-type DI to inhibit this biological effect of IgG APS.

Plasma was thawed on ice, meanwhile the Coagulometer (CA-50, Sysmex) was allowed to warm and reagents were prepared.

Patient antibodies were purified using Protein G IgG purification kit (Pierce), as described by manufacturer's instructions. IgA antibodies are purified using Jacalin beads (Pierce), as per manufacturer's instructions.

Patient antibody (500 μg/ml) was incubated with 50 μl normal lyophylised plasma and either B2GPI (25 μg/ml) or Domain I (25 μg/ml) for 15 minutes at 37° C. Plasma was then added to a total volume of 400 μl and incubated for a further 15 minutes at 37° C. before being tested as follows;

Plasma was dispensed into glass vials (200 μl×2) and reagents, either low [phospholipid] (LA sensitive) or high [phospholipid] (LA insensitive), were dispensed (200 μl each) into plastic 'cups' and allowed to warm for approximately 3 minutes at 37° C. before the assay was started. The vials of plasma were placed into the coagulation chamber and warmed to 37° C. for 3 minutes before the reagent (also pre-heated) was added. The chamber lid was closed and clot timing was begun. When the clot reached 50% the timing was stopped and recorded. The same assay is repeated for the Lupus Anticoagulant (LA) high [phospholipid] test using LA insensitive reagent. Analysis was performed by converting values to ratios compared to each other (i.e. Low [phosopholipid]:high [phospholipid]). A low phospholipid: high phospholipid (i.e. sensitive:insensitive) ratio value of >1.2 denoted LA activity. Data showing coagulometer assay results for wild type DI conjugates are shown in FIG. 8.

The assay containing excess phospholipid overcomes any LA effect in vitro, causing clotting times to revert to 'normal' values. Thus elongations in these times would indicate other factors influencing the assay, such as, dilution factor or other blood factor deficiencies etc. This assay can be used as an internal control for dilution of plasma.

Example 8

Competitive Inhibition ELISA for IgA Binding to β2GPI

Assays were carried out using identical methodology to Example 6 with the following alteration; an anti-human IgA secondary conjugated to HRP was used rather than an anti-human IgG secondary antibody. Results in FIG. 9 show that Non PEGylated DI inhibits IgA binding to β2GPI (column 2), which is retained to a large degree by the PEGylated conjugates (columns 4 to 7).

Example 9

In Vivo Mouse Blood Clot Model

In vivo analysis of inhibition of thrombus formation by DI was carried out in a similar manner to those described within Ioannou et al., 2009, Journal of Thrombosis and Haemostasis, 7: 833-842, In vivo inhibition of antiphospholipid antibody-induced pathogenicity utilizing the antigenic target peptide domain I of beta2-glycoprotein I: proof of concept.

C57BL/6 mice (The Jackson Laboratory, Bar Harbor, Me., USA) were used for these studies.

NHS IgG and APS IgG mean protein G purified antibody obtained from Normal Healthy Subjects or APS patients respectively.

Mouse Blood Vessel Pinch Model:

At time 0 h, 2 control groups were untreated, whereas 3 groups of mice were injected intraperitoneally with either recombinant wild-type DI (40 μg), PEGylated wild-type DI (20 μg) or PEG alone, in phosphate-buffered saline (PBS). After 60 min, 4 groups of mice were then treated intraperitoneally with 500 μg of APS IgG, while 1 group received 500 μg of NHS IgG, both in PBS. Both of these treatments were repeated at 48 h and 49 h respectively. The APS IgG dose was the minimal amount of APS IgG antibody required to increase thrombus size beyond two standard deviations (SDs) of the mean size induced by control NHS IgG post-injury. The APS IgG/DI molar ratios were 2.3:1, 1.15:1. At 72 h mice were anaesthetised and the femoral vein exposed. A pinch stimulus was applied and the thrombus formation was visualised using a transilluminator and measured electronically. Analysis of femoral vein thrombus dynamics in this mouse model has been described previously by Pierangeli et al., 1996, Thrombogenic properties of murine anti-cardiolipin antibodies induced by beta 2 glycoprotein 1 and human immunoglobulin G antiphospholipid antibodies, Circulation 1996; 94: 1746-51. For each group studied, five mice were employed, and for each mouse, three to five thrombi were successfully induced and mean area ($\mu m^2$) values were computed.

These results show (FIG. 10) that mice treated with IgG taken from patients with antiphospholipid syndrome (APS IgG) resulted in the formation of large blood clots in this model. In contrast, animals dosed with IgG from Normal Healthy Subjects (NHS IgG), resulted in smaller blood clot sizes. Treatment of the animals with APS IgG followed by PEGylated or non-PEGylated Wild Type-D1, prevented the formation of large blood clots, resulting in clot sizes similar to those observed within the NHS IgG treated mice.

The invention claimed is:

1. A conjugate of a domain I β2GP1 polypeptide with a water-soluble polymer, wherein the polymer is bound via two cysteine residues derived from a disulfide bridge in the domain I β2GP1 polypeptide, and wherein the domain I β2GP1 polypeptide comprises an amino acid sequence selected from the group consisting of: the amino acid sequence of SEQ ID NO: 2 and analogues thereof, and the amino acid sequence of SEQ ID NO: 3 and analogues thereof.

2. A conjugate as claimed in claim 1, wherein the domain I β2GP1 polypeptide comprises the amino acid sequence of SEQ ID NO: 2 or an analogue thereof.

3. A conjugate as claimed in claim 1, wherein the domain I β2GP1 polypeptide comprises the amino acid sequence of SEQ ID NO: 3 or an analogue thereof.

4. A conjugate as claimed in claim 1, in which polymer is bound via the $1^{st}$ and $3^{rd}$ cysteine residues of the domain I β2GP1 polypeptide sequence.

5. A conjugate as claimed in claim 1, in which polymer is bound via the $2^{nd}$ and $4^{th}$ cysteine residues of the domain I β2GP1 polypeptide sequence.

6. A conjugate as claimed in claim 1, in which the polymer is a polyalkylene glycol, a polyvinylpyrrolidone, a polyacrylate, a polymethacrylate, a polyoxazoline, a polyvinylalcohol, a polyacrylamide, a polymethacrylamide, a HPMA copolymer, a polyester, a polyacetal, a poly(ortho ester), a polycarbonate, a poly(imino carbonate), a polyamide, a copolymer derived from two or more alkylene oxides or from a poly(alkylene oxide) and a polyester, polyacetal, poly(ortho ester), or a poly(amino acid), a copolymer of divinylether-maleic anhydride and styrene-maleic anhydride, a polysaccharide, a protein, a poly(amino acid), or a copolymer of a saccharide or amino acid with ethylene oxide or methacrylic acid.

7. A conjugate as claimed in claim 6, in which said polymer is a polyalkylene glycol.

8. A conjugate as claimed in claim 7, in which said polymer is a polyethylene glycol.

9. A conjugate of a domain I β2GP1 polypeptide with a water-soluble polymer, which has the formula:

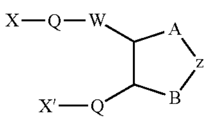

or

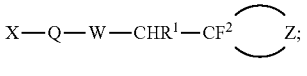

wherein the polymer is bound via two cysteine residues derived from a disulfide bridge in the domain I β2GP1 polypeptide;

in which one of X and X' represents a polymer and the other represents a hydrogen atom;

Q represents a linking group;

W represents an electron-withdrawing group or a group obtained by reduction of an electron-withdrawing group; or, if X' represents a polymer, X-Q-W' together may represent an electron withdrawing group;

A represents a $C_{1-5}$ alkylene or alkenylene chain;

B represents a bond or a $C_{1-4}$ alkylene or alkenylene chain;

$R^1$ represents a hydrogen atom or a $C_{1-4}$ alkyl group;

$R^2$ represents a hydrogen atom or a $C_{1-4}$ alkyl group; and

Z represents domain I β2GP1 polypeptide linked to the rest of the molecule via two thiol groups derived from a disulfide bond present in the domain I β2GP1 polypeptide.

10. A conjugate as claimed in claim 9, in which X is polyethylene glycol; X'Q- is H; and W is CO or CH.OH.

11. A conjugate as claimed in claim 10, in which A and B both represent $CH_2$.

12. A process for the preparation of a conjugate as claimed in claim 1, which comprises reacting the domain I β2GP1 polypeptide with a polymer conjugating reagent capable of binding to said polypeptide via two cysteine residues derived from a disulfide bridge in the domain I β2GP1 polypeptide.

13. A process as claimed in claim 12, in which the polymer conjugating reagent has the formula I or II:

(I)

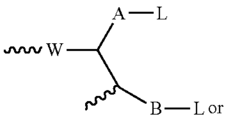

or (II)

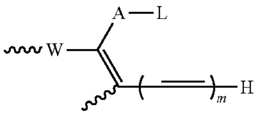

in which W represents an electron-withdrawing group; A represents a $C_{1-5}$ alkylene or alkenylene chain; B represents a bond or a $C_{1-4}$ alkylene or alkenylene chain; each L independently represents a leaving group; and m is 0 to 4; and in which the functional grouping (I) or (II) is bonded directly or indirectly to a water-soluble polymer at one of the points shown.

14. A process as claimed in claim 12, in which the polymer conjugating reagent has the formula I':

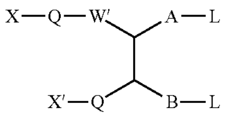

(I')

in which one of X and X' represents a water-soluble polymer and the other represents a hydrogen atom;

Q represents a linking group;

W' represents an electron-withdrawing group; or, if X' represents a polymer, X-Q-W' together may represent an electron withdrawing group;

A represents a $C_{1-5}$ alkylene or alkenylene chain;

B represents a bond or a $C_{1-4}$ alkylene or alkenylene chain; and each L independently represents a leaving group;

or (II'):

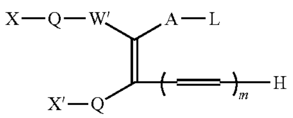

(II')

in which X, X', Q, W', A and L have the meanings given for the general formula I', and in addition if X represents a polymer, X' and electron-withdrawing group W' together with the interjacent atoms may form a ring, and m represents an integer 1 to 4;

or (III'):

$$X\text{-}Q\text{-}W'—CR^1R^{1'}—CR^2.L.L' \quad (III')$$

in which X, Q and W' have the meanings given for the general formula I', and either $R^1$ represents a hydrogen atom or a $C_{1-4}$ alkyl group, $R^{1'}$ represents a hydrogen atom, and each of L and L' independently represents a leaving group; or $R^1$ represents a hydrogen atom or a $C_{1-4}$ alkyl group, L represents a leaving group, and $R^{1'}$ and L' together represent a bond; or $R^1$ and L together represent a bond and $R^{1'}$ and L' together represent a bond; and $R^2$ represents a hydrogen atom or a $C_{1-4}$ alkyl group.

15. A process as claimed in claim 14, in which the polymer conjugation reagent is of the general formula I' or II' and includes the group:

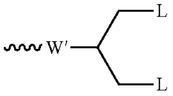

or

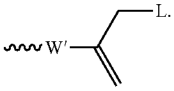

16. A process as claimed in claim 15, in which the polymer conjugation reagent has the formula:

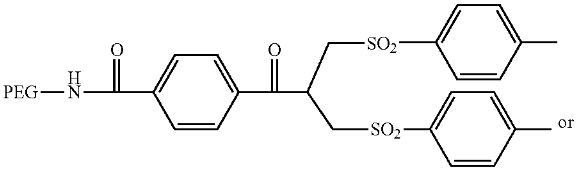

or

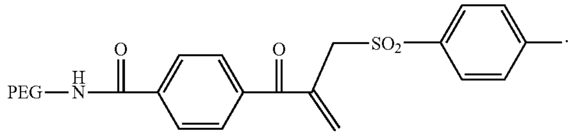

17. A process as claimed in claim 12, in which the polymer conjugating reagent contains the functional grouping:

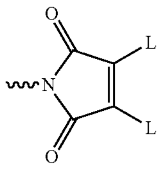

in which each L represents a leaving group; and in which the functional grouping is bonded directly or indirectly to a water-soluble polymer at the point shown.

18. A conjugate preparable by a process as claimed in claim 12.

19. A method of treating, preventing or alleviating antiphospholipid syndrome (APS) or sero-negative APS (SNAPS) which comprises the administration to a patient of a conjugate as claimed in claim 1.

20. A pharmaceutical composition comprising a conjugate as claimed in claim 1, together with a pharmaceutically acceptable carrier; optionally together with an additional active agent.

21. A conjugate as claimed in claim 9, wherein the domain I β2GP1 polypeptide comprises the amino acid sequence of SEQ ID NO: 2, an analogue of the amino acid sequence of SEQ ID NO: 2, the amino acid sequence of SEQ ID NO: 3, or an analogue of the amino acid sequence of SEQ ID NO: 3.

* * * * *

```
                         SEQUENCE LISTING


<160> NUMBER OF SEQ ID NOS: 3

<210> SEQ ID NO 1
<211> LENGTH: 326
<212> TYPE: PRT
<213> ORGANISM: Homo sapiens

<400> SEQUENCE: 1

Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60
```

-continued

```
Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Glu Gly Lys Trp Ser
            100                 105                 110

Pro Glu Leu Pro Val Cys Ala Pro Ile Ile Cys Pro Pro Pro Ser Ile
        115                 120                 125

Pro Thr Phe Ala Thr Leu Arg Val Tyr Lys Pro Ser Ala Gly Asn Asn
    130                 135                 140

Ser Leu Tyr Arg Asp Thr Ala Val Phe Glu Cys Leu Pro Gln His Ala
145                 150                 155                 160

Met Phe Gly Asn Asp Thr Ile Thr Cys Thr Thr His Gly Asn Trp Thr
                165                 170                 175

Lys Leu Pro Glu Cys Arg Glu Val Lys Cys Pro Phe Pro Ser Arg Pro
            180                 185                 190

Asp Asn Gly Phe Val Asn Tyr Pro Ala Lys Pro Thr Leu Tyr Tyr Lys
        195                 200                 205

Asp Lys Ala Thr Phe Gly Cys His Asp Gly Tyr Ser Leu Asp Gly Pro
    210                 215                 220

Glu Glu Ile Glu Cys Thr Lys Leu Gly Asn Trp Ser Ala Met Pro Ser
225                 230                 235                 240

Cys Lys Ala Ser Cys Lys Val Pro Val Lys Lys Ala Thr Val Val Tyr
                245                 250                 255

Gln Gly Glu Arg Val Lys Ile Gln Glu Lys Phe Lys Asn Gly Met Leu
            260                 265                 270

His Gly Asp Lys Val Ser Phe Phe Cys Lys Asn Lys Glu Lys Lys Cys
        275                 280                 285

Ser Tyr Thr Glu Asp Ala Gln Cys Ile Asp Gly Thr Ile Glu Val Pro
    290                 295                 300

Lys Cys Phe Lys Glu His Ser Ser Leu Ala Phe Trp Lys Thr Asp Ala
305                 310                 315                 320

Ser Asp Val Lys Pro Cys
                325


<210> SEQ ID NO 2
<211> LENGTH: 63
<212> TYPE: PRT
<213> ORGANISM: Homo sapiens

<400> SEQUENCE: 2

Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg
    50                  55                  60


<210> SEQ ID NO 3
<211> LENGTH: 63
<212> TYPE: PRT
<213> ORGANISM: Artificial Sequence
<220> FEATURE:
<223> OTHER INFORMATION: Human beta2 glycoprotein domain 1 variant
```

-continued

```
<400> SEQUENCE: 3

Gly Arg Thr Cys Pro Lys Pro Ser Gly Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg
    50                  55                  60
```